(12) United States Patent
Weisshaupt et al.

(10) Patent No.: US 9,138,231 B2
(45) Date of Patent: Sep. 22, 2015

(54) SURGICAL SYSTEM AND CONTROL PROCESS FOR A SURGICAL INSTRUMENT AND PROCESS FOR CONNECTING BODILY TISSUES

(75) Inventors: Dieter Weisshaupt, Immendingen (DE); Anton Keller, Duerbheim (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 352 days.

(21) Appl. No.: 13/516,083

(22) PCT Filed: Dec. 17, 2010

(86) PCT No.: PCT/EP2010/070018
§ 371 (c)(1),
(2), (4) Date: Aug. 22, 2012

(87) PCT Pub. No.: WO2011/083027
PCT Pub. Date: Jul. 14, 2011

(65) Prior Publication Data
US 2012/0323234 A1     Dec. 20, 2012

(30) Foreign Application Priority Data
Dec. 17, 2009   (DE) .......................... 10 2009 059 192

(51) Int. Cl.
*A61B 18/18* (2006.01)
*A61B 17/11* (2006.01)
(Continued)

(52) U.S. Cl.
CPC ......... *A61B 17/1114* (2013.01); *A61B 17/0643* (2013.01); *A61B 17/115* (2013.01); *A61B 18/1447* (2013.01); *A61B 17/32053* (2013.01); *A61B 18/1442* (2013.01); *A61B 2017/111* (2013.01); *A61B 2017/1132* (2013.01); *A61B 2018/0016* (2013.01); *A61B 2018/0063* (2013.01); *A61B 2018/00345* (2013.01);
(Continued)

(58) Field of Classification Search
None
See application file for complete search history.

(56) References Cited

U.S. PATENT DOCUMENTS

| 6,395,002 B1 | 5/2002 | Ellman et al. |
| 2003/0045811 A1 | 3/2003 | Hinchliffe et al. |

(Continued)

FOREIGN PATENT DOCUMENTS

| EP | 2 030 578 | 3/2009 |
| EP | 2 111 812 | 10/2009 |

(Continued)

OTHER PUBLICATIONS

International Search Report for International Application No. PCT/EP2010/070018 dated Mar. 18, 2011.
(Continued)

*Primary Examiner* — Brian T Gedeon
(74) *Attorney, Agent, or Firm* — RatnerPrestia

(57) ABSTRACT

The invention relates to improving a surgical system for connecting bodily tissues, comprising a surgical instrument having two tool elements displaceable relative to each other, each comprising an HF electrode defining a minimum distance from each other, opposite each other, and facing one another in an approach setting of the tool elements, wherein in order for simple and secure connecting of the tissue parts to be connected to each other, the invention proposes that at least one of the HF electrodes is divided into at least two electrode segments and that the at least two electrode segments are electrically insulated from each other.

19 Claims, 19 Drawing Sheets

(51) Int. Cl.
  *A61B 17/064* (2006.01)
  *A61B 17/115* (2006.01)
  *A61B 17/3205* (2006.01)
  *A61B 18/14* (2006.01)
  *A61B 18/00* (2006.01)
  *A61B 18/12* (2006.01)

(52) U.S. Cl.
  CPC ............... *A61B2018/00404* (2013.01); *A61B 2018/00619* (2013.01); *A61B 2018/126* (2013.01); *A61B 2018/1412* (2013.01); *A61B 2018/1455* (2013.01); *A61B 2018/1467* (2013.01)

(56) References Cited

U.S. PATENT DOCUMENTS

2003/0069571 A1  4/2003  Treat et al.
2006/0064086 A1  3/2006  Odom
2008/0243121 A1  10/2008  Takashino et al.
2009/0043305 A1  2/2009  Brodbeck et al.
2011/0125176 A1* 5/2011  Yates et al. .................... 606/170

FOREIGN PATENT DOCUMENTS

JP      2009-261907 A    11/2009
WO      WO 2006/021269   3/2006
WO      WO 2009/022614   2/2009

OTHER PUBLICATIONS

Canadian Examination Report issued in related Canadian Application No. 2,784,111, dated May 2, 2014.
Examination Report issued in related Japanese Application No. 2012-543776, drafted on Jul. 26, 2013.

* cited by examiner

SURGICAL SYSTEM AND CONTROL PROCESS FOR A SURGICAL INSTRUMENT AND PROCESS FOR CONNECTING BODILY TISSUES

CROSS REFERENCE TO RELATED APPLICATIONS

This application is the national phase entry under 35 U.S.C. §371 of International Application No. PCT/EP2010/070018, filed Dec. 17, 2010, and claims the benefit of priority of German Application DE 10 2009 059 192.3, filed Dec. 17, 2009, the contents of both applications being incorporated by reference herein for all purposes.

FIELD OF THE INVENTION

The present invention pertains to a surgical system for connecting body tissues, comprising a surgical instrument with two tool elements, which are movable in relation to one another and which comprise an RF electrode each, which define a minimal distance from one another, lie opposite one another and point towards one another in a position of proximity of the tool elements.

The present invention also pertains to a control process for a surgical instrument with two tool elements, which comprise an RF electrode each and lie opposite one another and point towards one another in a position of proximity.

The present invention also pertains to a process for connecting two body tissues, in which the two body tissues to be connected are held in contact with one another between two RF electrodes.

BACKGROUND

For connecting body tissue it is known, especially in end-to-end anastomoses, to connect the tissues to be connected to one another by means of clip suture devices by means of clips. It is also known to coagulate tissue with RF current, for example, by applying an RF current to the tissue between two RF electrodes.

The use of clip suture devices has especially the drawback that clips are left behind in the body of the patient. A tissue sealing by means of RF current is advantageous over the clipping together of tissue. However, it is difficult to control process parameters precisely when sealing with RF current.

SUMMARY

Therefore, the object of the present invention is to perfect a surgical system for connecting body tissues, a control process for a surgical instrument as well as a process for connecting two body tissues, such that a simple and reliable connection of the tissues to be connected to one another is made possible.

This object is accomplished according to the present invention by a surgical system of the type described in the introduction in that at least one of the RF electrodes is divided into at least two electrode segments, and in that the at least two electrode segments are electrically insulated from each other.

The division of at least one of the RF electrodes into one or more electrode segments has especially the advantage that the process parameters for connecting, also called sealing or welding below, the tissues to be connected to one another, can be significantly more easily controlled. The smaller the surfaces between which the RF current is applied, the more easily can the process parameters be controlled. In particular, the temperature, pressure as well as tissue impedance have a considerable effect on the connection result. For example, it is thus also possible to adjust the process parameters optimally to the tissue quality and especially also automatically. Moreover, other than when using a clip suture device, no clips, which remain behind as foreign bodies in the body, are needed. The electrode segments dividing the RF electrode or RF electrodes especially make possible a current feed of the RF electrode in segments, such that the tissues to be connected to one another can be welded or sealed to one another in segments. A sequential current feed, which is possible due to the segmenting of the RF electrodes, makes it possible to introduce less energy into the tissues during the connection or sealing process than in comparable, unsegmented RF electrodes. Segmenting also has the advantage that between areas, connected by RF current feed, of the tissues to be connected to one another, tissue areas remain unchanged and essentially undamaged, such that starting from these areas, new cell growth is made possible, which, in addition to the connection brought about by the RF current, makes possible a permanent connection of the tissues by means of a growing together of same.

To be able to improve the controllability of the process parameters even further, it is advantageous if each of the RF electrodes is divided into at least two electrode segments, which are electrically insulated from each other. In the sense of this application, at least two electrode segments means two or more electrode segments, i.e., especially three, four, five, six, seven, eight, nine, ten, eleven or twelve. However, even more are conceivable, and even 20, 25, 30 or 40 electrode segments depending on the size of the tool elements.

Advantageously, at least one of the RF electrodes is divided into a plurality of electrode segments. In the sense of this application, a plurality of electrode segments is defined as more than two electrode segments, which make possible an even further improved controllability of the process parameters.

Electrode segments lying opposite one another and pointing towards one another in the position of proximity advantageously form a pair of electrode segments. Such a pair of electrode segments can, for example, be controlled as a unit. In this way, especially local edge conditions in the area of the two electrode segments can be optimally taken into consideration, especially temperature, pressure and tissue impedance of tissue held between the pair of electrode segments.

To be able to conduct the RF current in an especially defined manner for connecting the tissue from one electrode segment of the pair of electrode segments to the associated electrode segment, it is advantageous when the electrode segments forming the pair of electrode segments are geometrically similar.

The function of the system can be further perfected, for example, in that the electrode segments forming the pair of electrode segments are the same size or essentially the same size. In this way, current densities can especially be optimally predetermined.

The at least two electrode segments can be embodied in an especially simple manner when they are designed as strip-shaped or essentially strip-shaped.

According to a preferred embodiment, provisions may be made for each of the tool elements to define a tool element surface and for the RF electrode to form a part of the tool element surface. This embodiment makes it possible to design the tool elements as practically without protrusion.

The tool element surface is preferably flat. Manufacture of the instrument as well as its cleanability are thereby markedly simplified.

Depending on the intended use of the surgical system, i.e., especially depending on the tissues to be connected, it may be advantageous if the tool element surface is designed as rectangular, circular or U-shaped. In particular, a circular tool element surface makes it possible to perform end-to-end anastomoses in a simple manner.

It is advantageous when the at least two electrode segments are arranged next to one another in at least two rows of electrodes. At least two rows of electrodes make it possible to prepare at least two connecting lines running next to one another. Consequently, an improved connection and especially an optimal sealing of the connection points between the tissues can be achieved. In particular, completely or essentially undamaged cells may remain behind between the rows of electrodes even after connecting the tissues by means of RF current, from which new cell growth can originate. In addition to the connection of tissues by welding, this makes possible, in the long term, a permanent connection of the tissues due to the growing together of intact cells.

To prevent short-circuits, it is advantageous when the at least two rows of electrodes are electrically insulated from each other. Furthermore, it is thus also possible to apply RF current to the rows of electrodes separately from one another to make a connection between the tissues specifically one after the other or even simultaneously.

Each row of electrodes preferably comprises at least two electrode segments, which are electrically insulated from each other. Thus, at least one sequential current feed can be accomplished.

According to another preferred embodiment, provisions may be made for at least one electrode segment to have a first electrode segment section, which is part of a first row of electrodes, and a second electrode segment section, which is part of a second row of electrodes. In this way, a two-row tissue connection can be produced, especially comprising or defining two connecting lines, whereby an even better overlap between the two connecting lines is achieved by the especially embodied electrode segment sections, which results especially in an improved sealing of the tissue connection.

In order to be able to form desired connecting lines, it is advantageous when the at least two rows of electrodes are designed as linear and/or curved. This means especially that they may be designed as completely linear or completely curved or linear and curved in sections.

To be able to connect tissues to one another in a circular manner, which is especially necessary for end-to-end anastomoses, it is advantageous when the at least two rows of electrodes have a self-contained circular design.

So that each electrode segment can be fed current individually as needed, it is advantageous when each electrode segment is connected in an electrically conductive manner to a terminal contact. The terminal contact may in turn be connected to other terminal contacts or be connected or connectable directly to a current source.

Further, it may be advantageous when the RF electrode defines an electrode center line and when electrode segments, adjacent to one another, are arranged offset to one another in a direction defined by the electrode center line. Due to the offset arrangement of the electrode segments, an optimal overlap of tissues connections or tissue connection lines, which are produced by means of the RF electrodes, will be achieved in a direction transverse to the electrode center line. Consequently, a risk of leaks can be specifically minimized.

According to another preferred embodiment, provisions may be made for the at least one RF electrode divided into at least two electrode segments to define an electrode length and for each of the at least two electrode segments to define a segment length, which is shorter than the electrode length. Due to this construction, it can be especially guaranteed that only one section of the tissues to be connected to one another can be connected to each electrode segment, which is shorter than the total length of the RF electrode.

To improve a sealing of a connection site between two tissues produced by means of the surgical system, it is advantageous when the sum of all segment lengths is greater than the electrode length. This guarantees at least partly an overlap of tissue connections made with the electrode segments.

In order to be able to connect the instrument in a simple and reliable manner to an RF generator or to another suitable RF current source, it is advantageous when the instrument comprises at least two RF terminal contacts, which are connected or can be connected in an electrically conductive manner to the at least two electrode segments.

To be able to grip and possibly hold tissue between the two tool elements during the connection process, it is advantageous when the tool elements are designed as pivotable and/or displaceable in relation to one another. All in all, a movable arrangement of the tool elements in relation to one another is thus desirable.

It is advantageous when the tool elements form distal ends or end areas of branches mounted pivotably or movably to one another. This embodiment especially makes possible the design of a tong-shaped instrument, which makes possible the clamping holding of the tissues to be connected between the tool elements.

According to another preferred embodiment, provisions may be made for the instrument to have a shaft, at the distal end of which is arranged or formed at least one of the tool elements. In this way, the instrument can be designed as especially compact. Further, the stability of the instrument can be increased all in all due to the arrangement or design of at least one of the tool elements at the distal end of the shaft. It is also especially possible to design one of the tool elements in a simple manner as fixed in relation to the shaft.

It is advantageous when a first tool element comprises an edge surface of the shaft pointing in the distal direction or essentially in the distal direction. For example, a distal end of the shaft can thus be simply pressed or held against a tissue, which will be connected to another tissue. Moreover, a defined tool element surface can thus also be predetermined in a simple and reliable manner.

According to another preferred embodiment of the present invention, provisions may be made for a second tool element to comprise an electrode element that is movable in the shaft direction and can be moved in the direction towards the first tool element and away from same. This embodiment makes it possible, for example, to move the two tool elements in relation to one another, such that tissues to be connected to one another can be held in a defined manner between them and can be connected to one another by means of corresponding application of RF current.

It is advantageous when contact members pointing in the direction of the second tool element, which can be brought into electrically conductive contact with the electrode segments of the second tool element in a tissue connection position and are spaced away from the electrode segments of the second tool element in a tissue gripping position, protrude at the shaft and/or the first tool element. With the contact members, it is possible to contact and to connect the electrode segments of the second tool element by means of an electrically conductive connection to a current source, for example, an RF generator, for example, provided in the shaft. Further, the suggested design has the advantage that a contact between the electrode segments of the second tool element and the contact members can only be made in the tissue connection position, such that the electrode segments of the second tool element cannot be fed current inadvertently in the tissue gripping position. Managing of the surgical system is consequently altogether even more reliable.

So that the tool elements can be moved in relation to one another in a simple manner, it is advantageous when the instrument comprises an actuating means for moving the tool elements in relation to one another.

To further improve the manageability of the surgical instrument, the actuating means is arranged or formed preferably at a proximal end of the instrument. For example, if the instrument has a shaft, this can be inserted through a body opening into the interior of the body, whereby the tool elements can then be actuated in relation to one another by means of the actuating means, which preferably is still protruding from the body of the patient. All in all, an endoscopic or minimally invasive surgical instrument can thus be designed in a simple manner.

The manageability of the instrument can especially be improved for a surgeon in that the actuating means comprises two actuating members which are pivotable in relation to one another and which are in operative connection with at least one of the tool elements for transmitting an actuating force for moving the at least one tool element in relation to the other tool element. The actuating members may also basically be designed as movable only in relation to one another, i.e., as an alternative, for example, to a pivotable arrangement, they may also be arranged as displaceable or as pivotable and displaceable to one another.

According to another preferred embodiment, provisions are advantageously made for the instrument to comprise an RF cutting element for cutting tissue. The provision of an RF cutting element, which may be, for example, part of a cutting means of the instrument, especially makes it possible to prepare tissues connected to one another in a desired manner. For example, this may be the case when end-to-end anastomoses are produced with the system, whereby free ends of tubular tissue can be connected in a circular manner by means of the instrument and then protruding tissue can be cut by means of the cutting element or cutting means.

The RF cutting element preferably has a cutting edge, which defines a cutting plane that is sloped in relation to a longitudinal axis of the instrument, especially in the area of the RF cutting element. Due to the sloped cutting plane, for example, RF current can be conducted via the cutting element to cut tissue. The thus designed cutting edge then has a minimal distance to a counterelectrode only in a small area, which defines a plane transverse to the longitudinal axis of the instrument. Thus, a cutting spark can be produced in a defined manner in the area of the shortest distance between the RF cutting element and a corresponding counterelectrode, whereby the cutting spark can then travel along the sloped cutting edge in a defined manner.

The cutting edge is advantageously closed in a circular shape to be able to make a circular cut in a simple and reliable manner.

So that RF current can be applied to the RF cutting element in a defined manner, it is advantageous when the instrument has an RF cutting terminal connected in an electrically conductive manner to the RF cutting element. Especially in such an embodiment, RF current can be applied to the RF cutting element in a defined manner for cutting tissue, preferably independently and separately in terms of time from applying an RF current to the electrode segments for connecting the tissues to one another.

It is advantageous when the cutting element is arranged as movable in relation to at least one of the tool elements. This makes it possible, for example, to move the cutting element in relation to the tool elements, such that it cannot come into contact with the tissues to be connected to one another when these are connected to one another by means of the electrode segments embodied on the tool elements. Rather, it is thus possible, for example, to bring the cutting element only after connecting the tissues into a position, in which these can be cut in the desired manner and/or entirely or partly severed.

In order to be able to apply RF current to the RF instrument in a desired manner, the surgical system preferably comprises at least one RF current generator, which can be connected selectively in an electrically conductive manner to the RF electrodes and/or to the cutting element. Thus, the optimal current for connecting or cutting tissue, respectively, can especially be adjusted.

According to another preferred embodiment, provisions may be made for the system to comprise at least one control and/or regulating means with a switching means for the sequential application of RF current to the electrode segments of at least one RF electrode. Optionally, RF current may also be applied to another RF electrode with the control and/or regulating means. Due to the switching means designed in the manner described, RF current may be applied especially to the electrode segments of an RF electrode one after the other, i.e., in a sequential succession in order to connect the tissues to be connected to one another in sections.

It is advantageous when the surgical system comprises a control and/or regulating means with a switching means for the simultaneous application of RF current to at least two electrode segments of at least one RF electrode. In this way, the connection or sealing process can be accelerated or carried out faster, since two tissues to be connected to one another can be connected to one another simultaneously along two sections. It is also especially conceivable to apply RF current to two electrode segments each simultaneously and other electrode segments then sequentially.

To prevent short-circuits, when RF current is applied to two electrode segments simultaneously, it is advantageous when at least one other electrode segment is arranged between the at least two electrode segments.

It is advantageous when the switching means is designed for switching at least one RF output of the at least one current generator. Two, three or even more RF outputs may also be provided, which can be controlled and/or regulated by the switching means, in order to apply RF current in a desired intensity, for example, specifically to individual electrode segments of the RF electrodes.

It is advantageous when the surgical system comprises an RF generator, which can be connected selectively in an electrically conductive manner to the RF electrodes or to the cutting element and comprises the control and/or regulating means. In this way, several functions of the system can be accommodated in one device, which improves both its manufacture and its manageability.

Advantageously, the control and/or regulating means is designed such that a current feed intensity and/or a duration of current feed can be adjusted for the individual electrode segments. In this way, process parameters such as temperature, pressure as well as tissue impedance can be kept directly or indirectly within the desired range by means of the control and/or regulating means.

In order to prevent a too intense heating of the tissues to be connected to one another, which would result in destruction of cells, it is advantageous when the control and/or regulating means comprises a temperature measuring means for measuring an electrode segment temperature and/or a tissue temperature.

Furthermore, it is advantageous when the control and/or regulating means comprises an impedance measuring means for measuring the tissue impedance of tissue held between the tool elements. The determination of the tissue impedance makes it possible to regulate the current or RF generator, and especially the power provided by same, depending on the value thereof. In this way, the energy for connecting the tissues to be introduced into same can be regulated in a simple and reliable manner. The RF electrodes can especially be used for measuring the tissue impedance. A measurement may thus be taken between individual electrode segments which lie opposite one another. Preferably, the tissue impedance is measured when the RF electrodes are particularly currentless. It is especially advantageous to measure the tissue impedance in the pauses when switching the polarity of the RF current. Thus, the change in the tissue can be monitored well and practically in real time and further energy input can be stopped or specifically further permitted.

The object stated in the introduction is further accomplished according to the present invention with a control process of the type described in the introduction in that at least one of the RF electrodes is divided into at least two electrode segments, in that at least two electrode segments are electrically insulated from each other, in that RF current is applied to one of the at least two electrode segments and at least one other of the at least two electrode segments is left currentless.

With such a control process it is possible to feed current to the at least two electrode segments at least partly sequentially, i.e., one after the other. Consequently, current densities needed for tissue connection can be reduced, which has a positive effect on process parameters such as temperature, pressure and tissue impedance as well as their controllability. The tissues to be connected to one another may in this way be connected to one another in a markedly sparing manner. By means of corresponding current feed of electrode segments, different sections of the tissues to be connected to one another can then be connected to one another one after the other.

To reduce the time needed for connecting the tissues, it is advantageous when at least two electrode segments are fed current simultaneously. Preferably, these do not lie directly adjacent to one another. Thus, short-circuits and undesired temperature elevations can be prevented in certain tissue areas.

Electrode segments that are adjacent to one another are preferably fed current one after the other. In this way, sections of the tissues to be connected to one another, which are demarcated clearly and unambiguously from one another, can be connected to one another in a defined manner.

The object stated in the introduction is further accomplished according to the present invention by a process for connecting two body tissues of the type described in the introduction in that the two body tissues to be connected are held in contact with one another between two RF electrodes, at least one of which is divided into at least two electrode segments, which electrode segments are electrically insulated from each other, and in which the body tissues are welded to one another by means of RF current along a connecting line by applying RF current to the at least two electrode segments.

The suggested process offers a simple alternative to using clip suture devices and makes the use of clips and thus possible risks when same are left behind in the body of the patient superfluous. By means of the process described, two tissues with still partly vital body cells can be connected to one another especially in a defined and reliable manner.

To prevent short-circuits and cell damage, it is advantageous when RF current is applied to the at least two electrode segments one after the other.

So that a surgeon can connect the two tissues to one another along a defined connecting line, it is advantageous when the RF electrodes predetermine the connecting line. Thus, already when placing an instrument at the body tissues to be connected to one another, it may define along which line these will be connected to one another.

BRIEF DESCRIPTION OF THE DRAWING FIGURES

The following description of preferred embodiments of the present invention is used for a detailed explanation in connection with the drawings. In the drawings, FIG. 1 shows a schematic general view of a surgical instrument for connecting body tissues;

DETAILED DESCRIPTION

Figure 1:
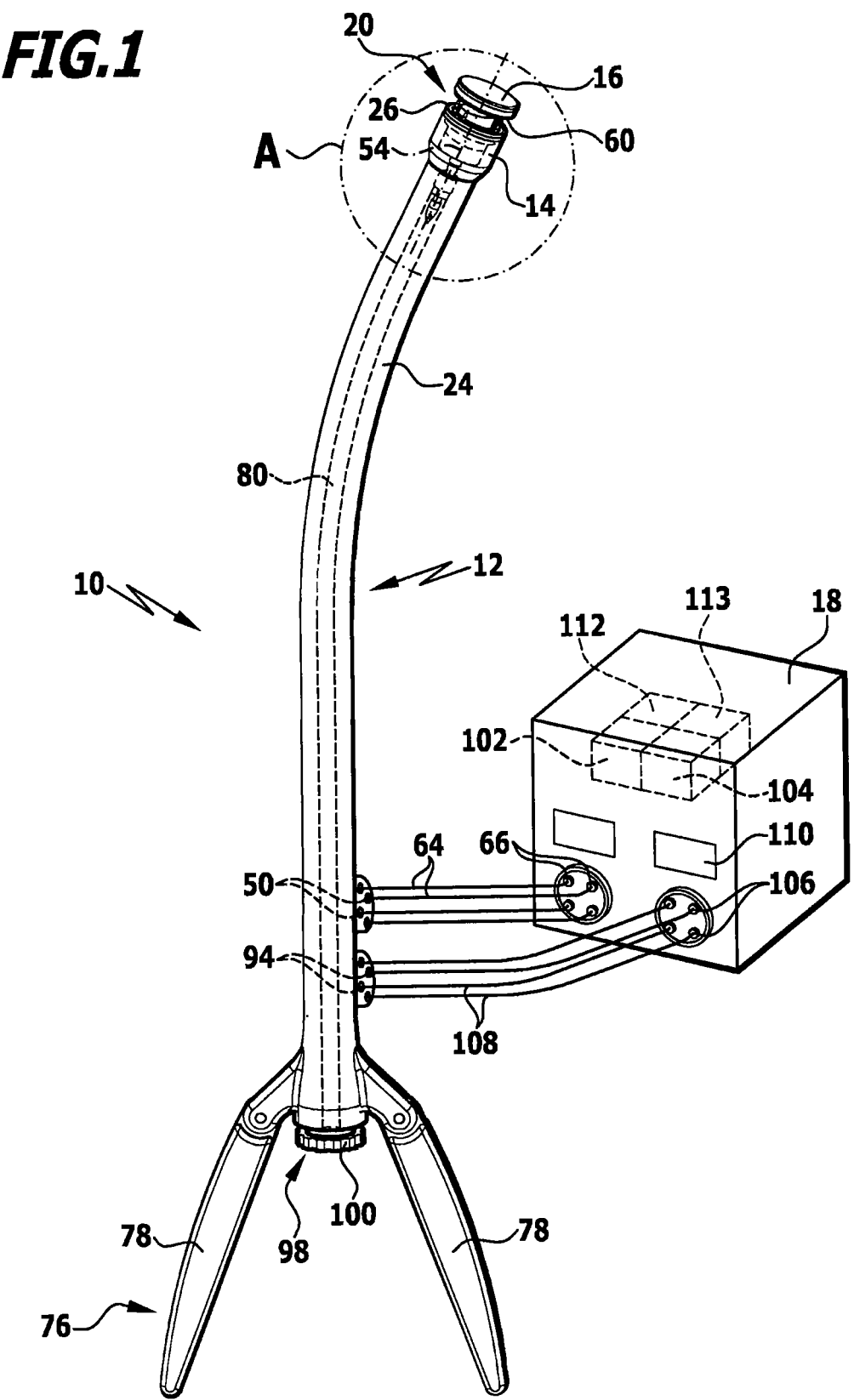

A surgical system for connecting body tissue is schematically shown in FIG. 1 and is designated as a whole with reference number 10. It comprises a surgical instrument 12 with two tool elements 14 and 16 which are movable in relation to one another. Further, the system 10 comprises a current generator in the form of an RF current generator 18, which can be connected to the instrument 12 in another manner described in detail below.

The tool elements 14 and 16 form a part of a connecting means, provided as a whole with reference number 20, for connecting body tissue. The first tool element 14 comprises an edge surface 22, pointing in the distal direction, of an elongated, sleeve-like shaft 24 of the instrument 12. Thus, the first tool element is arranged or formed at a distal end 26 of the instrument 12.

The first tool element 14 comprises an RF electrode 28. It is divided into at least two electrode segments 30, into four electrode segments 30 in the exemplary embodiment schematically shown in FIGS. 2 through 5, which are electrically insulated from each other. The electrode segments 30 are designed as strip-shaped or essentially strip-shaped. The first tool element 14 defines a tool element surface 32 such that the RF electrode 28 forms a part of same. All in all, the tool element surface 32 is designed as flat and circular.

The four electrode segments 30 define two rows of electrodes 34 and 36. Each row of electrodes comprises a part of the four electrode segments 30 each. As can be seen, for example, in FIG. 5, each electrode segment 30 has a first electrode segment section 38, which forms a part of the first row of electrodes 34, and a second electrode segment section 40, which forms a part of the second row of electrodes 36. The two rows of electrodes 34 and 36 have an overall curved design, whereby the electrode segment sections 38 and 40 define electrically conductive circular ring sections each. All in all, the at least two rows of electrodes, which are defined by four electrode segment sections 38 or 40 each, have a self-contained circular design. To be able to contact the electrode segments 30 in a desired manner, each electrode segment 30 is connected in an electrically conductive manner to a terminal contact 42 which is arranged in a connection area between the electrode segment sections 38, 40. Even after tissues are connected by RF current feed, completely or essentially undamaged cells, from which new cell growth can start, remain behind between the rows of electrodes. In the long term, this makes possible in addition to connecting tissues by welding a permanent connection of the tissues due to the growing together of intact cells.

RF electrode 28 defines an electrode center line 44 running between the electrode segment sections 38 and 40. Therefore, electrode segments 30 which are adjacent to one another are arranged offset to one another in a direction defined by the electrode center line 44. All in all, the RF electrode 28 divided into four electrode segments 30 defines an electrode length 46, whereby each of the four electrode segments 30 defines a segment length 48 that is shorter than the electrode length 46. As shown, for example, in FIG. 5, electrode segments 30 extend over an angle range of approx. 140° and thus have a length that corresponds to approximately 40% of the electrode length 46. Thus, the sum of all segment lengths 48 is, however, also approx. greater by a factor of 1.6 than the electrode length 46.

RF terminal contacts 50, which are connected in an electrically conductive manner, for example, via lines running in the shaft, to the electrode segments 30, are arranged in the area of a proximal end of the shaft 24. The number of RF terminal contacts 50 preferably corresponds to the number of electrode segments 30, i.e., four RF terminal contacts 50 for the four electrode segments 30 of the first tool element 14.

The second tool element 16 is designed as essentially disk-like and comprises an electrode element 52, which can be moved in the direction of the first tool element 14 and away from same as well as parallel to a longitudinal axis 54 of the shaft 24 in the area of the tool elements 14, 16 which defines a shaft direction 56. The tool elements 14, 16 are arranged displaceable in relation to one another, i.e., a distance 58 between the tool element surface 32 of the first tool element 14 and a tool element surface 60 of the second tool element 16 is variable.

The electrode element 52 comprises an RF electrode 29, which corresponds to the RF electrode 28 in its design. This means that it also comprises four electrode segments 31, which do not protrude over the tool element surface 60. Two rows of electrodes 35 and 37 are likewise defined, whereby first electrode segment sections 39 define the row of electrodes 35 and second electrode segment sections 41 define the row of electrodes 37. Terminal contacts 43 are likewise provided, which conductively connect an electrode segment section 39 to an electrode segment section 41 each for forming an electrode segment 31. RF electrodes 28 and 29 are designed as mirror-symmetrical to a mirror plane running at right angles to the longitudinal axis 54 between the tool element surfaces 32 and 60. In this way, pairs of electrode segments 62 are defined by an electrode segment 30 each and the corresponding electrode segment 31 lying opposite same. All in all, the exemplary embodiment shown in FIGS. 1 through 5 thus comprises four pairs of electrode segments 62. The electrode segments 30, 31 are not only geometrically similar, but also have the same size or essentially the same size.

Figure 4:
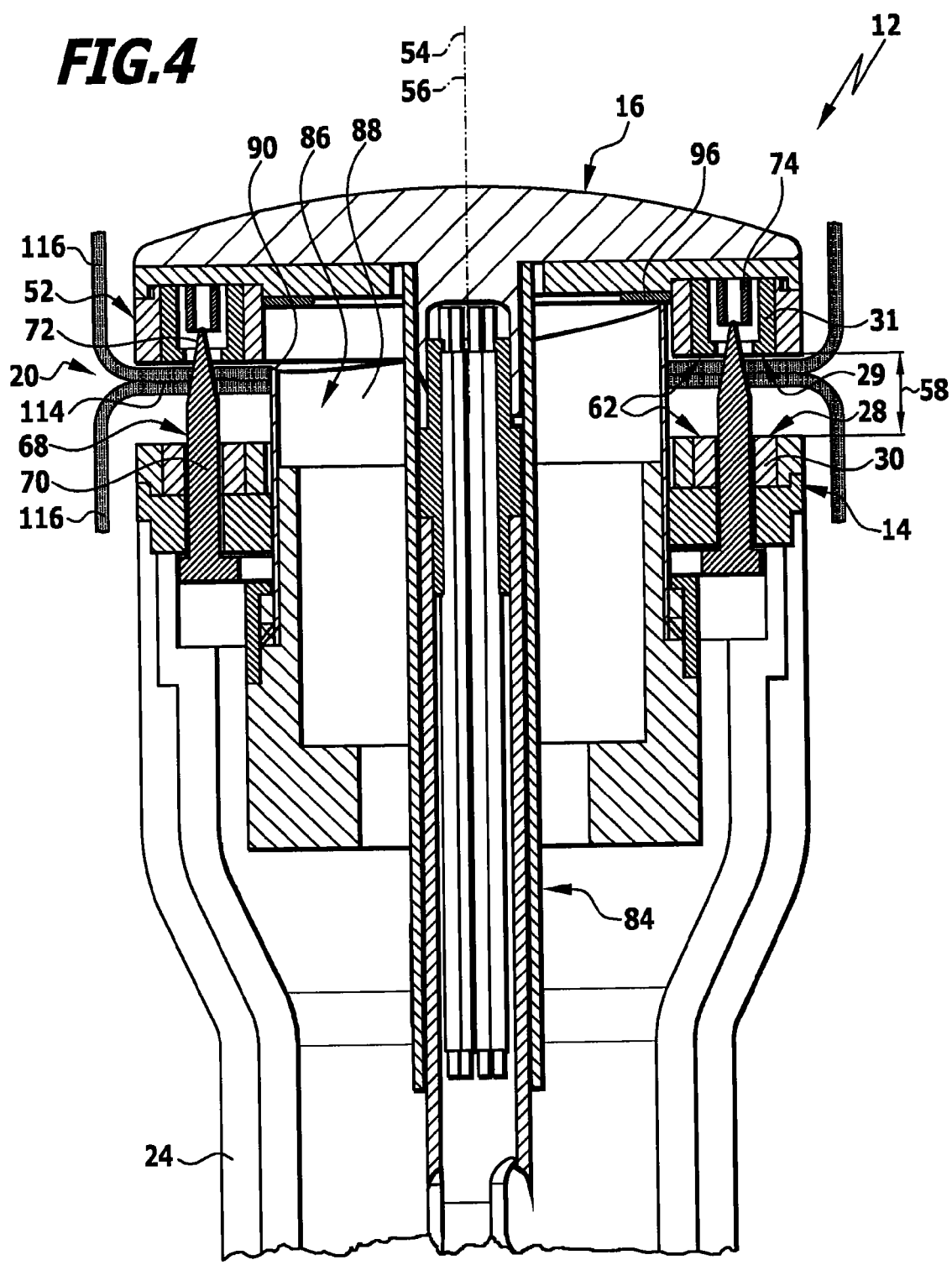
FIG. 4 shows a view similar to FIG. 3 when welding the tissues for creating an end-to-end anastomosis.
Figure 5:
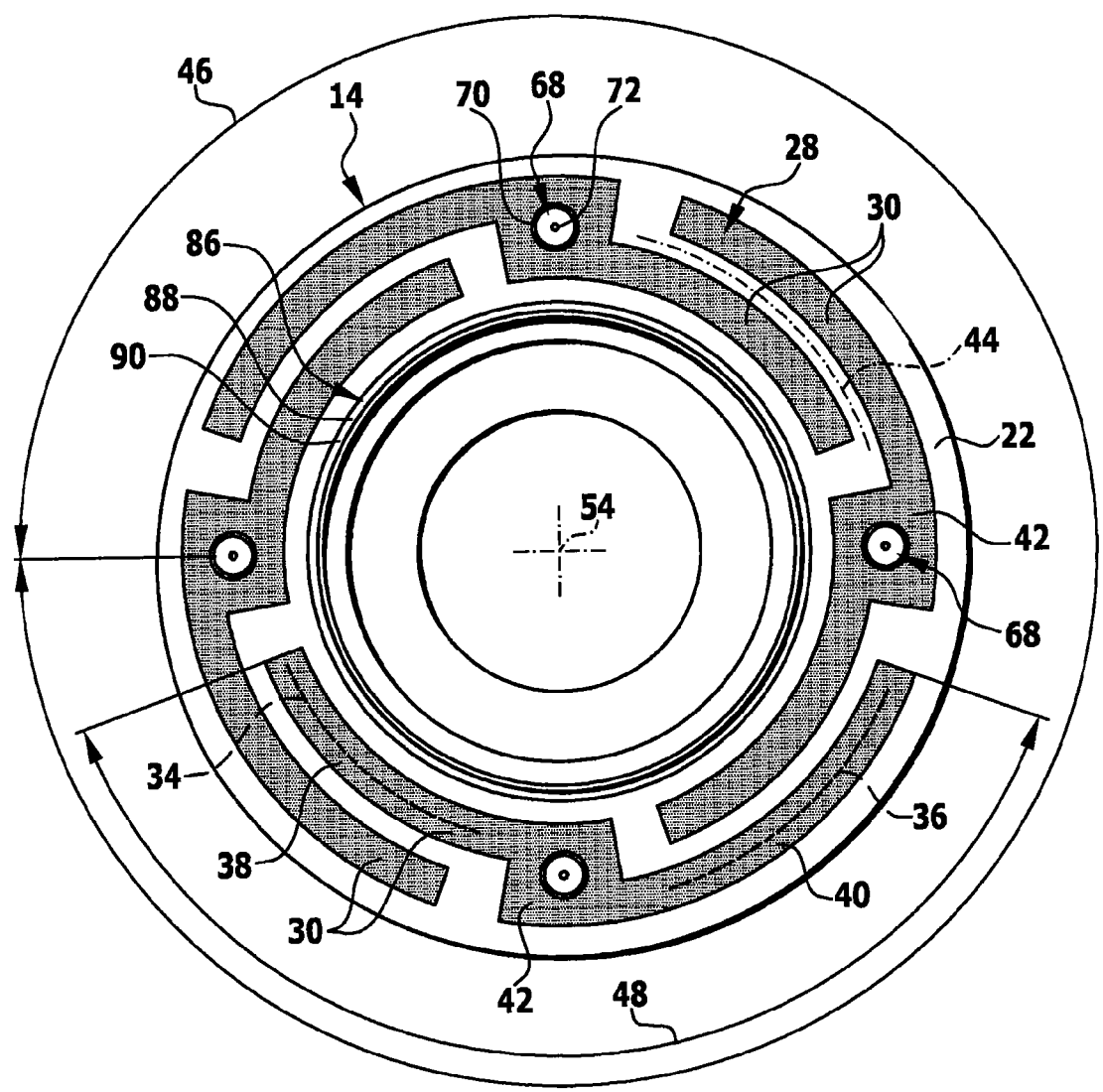
FIG. 5 shows a top view of a tool element surface with an RF electrode divided into four electrode segments.

The RF electrodes 28, 29 define a minimal distance 58 from one another in a position of proximity of the tool elements 14, 16. The position of proximity is schematically shown in FIG. 4. In the position of proximity, the RF electrodes 28 and 29 lie opposite one another and point towards one another.

The electrode segments 31 can be connected in an electrically conductive manner to another four RF terminal contacts 50, of which only two are shown in FIG. 1 for the sake of clarity. The RF terminal contacts 50 may be connected to corresponding contacts 66 of the RF current generator 18 by means of corresponding connecting lines 64. As already explained, the RF terminal contacts 50 are directly connected in an electrically conductive manner to the electrode segments 30. To be able to connect the RF terminal contacts 50 to the electrode segments 31, contact members 68, which have a short cylindrical section 70 and a cone-shaped section 72 defining a free end, are arranged projecting at the shaft 24 or at the first tool element 14 pointing in the direction of the second tool element 16. In a tissue connection position, as it is schematically shown, for example, in FIG. 4, i.e., in a position, in which tool elements 14 and 16 are located in the position of proximity, the free ends of the sections 72 of the contact members 68 extend into corresponding sleeve-like mounts 74 of the electrode element 52 and are in electrically conductive contact with same. Contact members 68 are in turn connected to the RF terminal contacts 50 along the shaft 24 via electrical lines (not shown). The mounts 74 are in turn connected in an electrically conductive manner to the terminal contacts 43. In this way, an electrically conductive contact between the RF terminal contacts 50 and the electrode segments 31 can also be made in the proximity position or tissue connection position.

Of course, contact members 68, which pass through the electrode segments 30 in the area of their terminal contacts 42, are insulated from same, so that no short-circuits can occur. For this purpose, the sections 70 of the contact members 68 are preferably provided with an electrically conductive coating or shell.

In order to be able to move the tool elements 14, 16 of the instrument 12 in relation to one another, an actuating means 76 is arranged at a proximal end or end area of the instrument 12. The actuating means 76 comprises two actuating members 78, which are pivotable in relation to one another and which are movably coupled with a force transmission member 80 mounted movably in the interior of the shaft, such that as a result of the pivoting movement of the actuating members 78, the force transmission member is movable in the distal or proximal direction.

Figure 2:
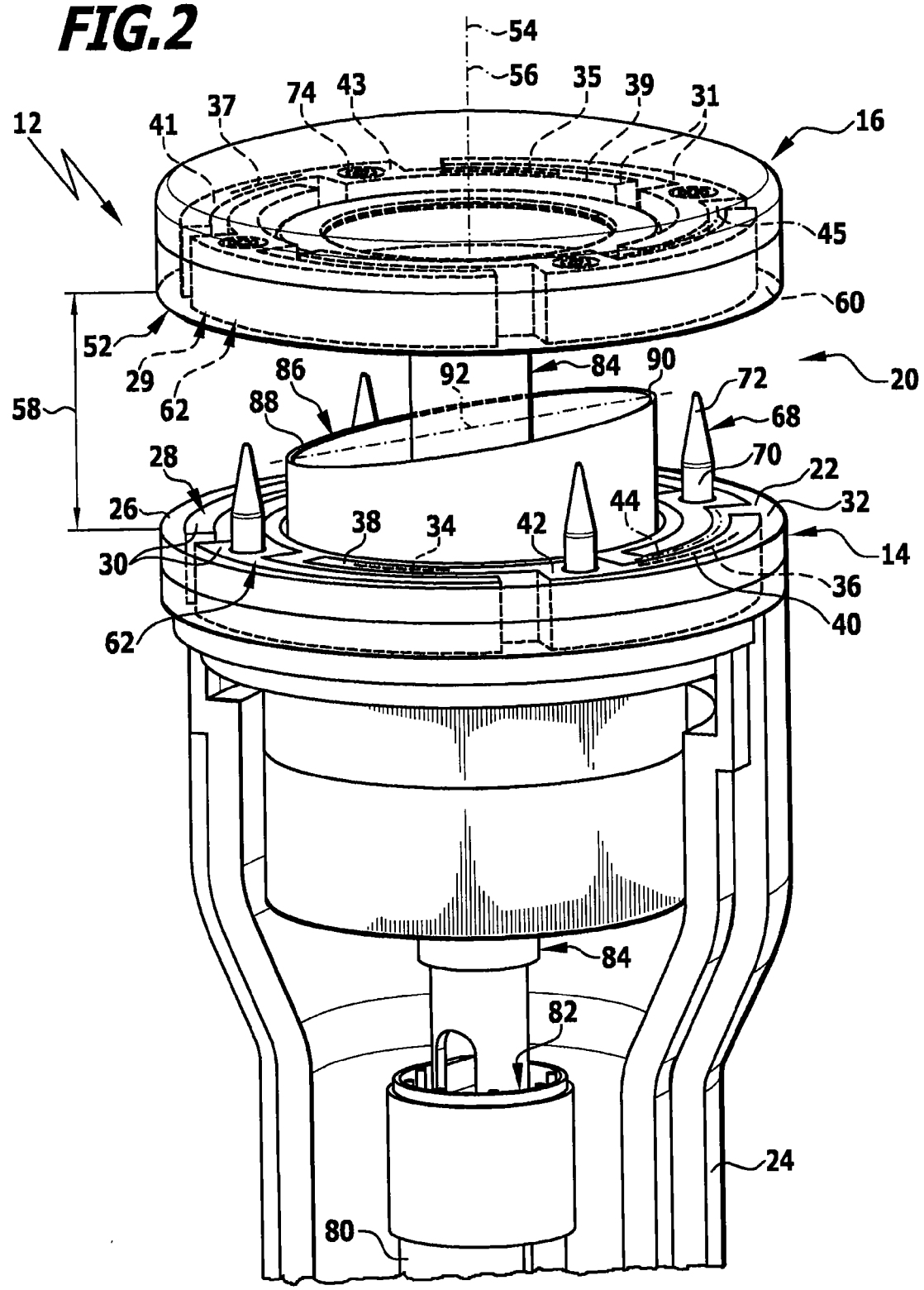
FIG. 2 shows an enlarged, perspective, partly sectional and open view of area A in FIG. 1.
Figure 3:
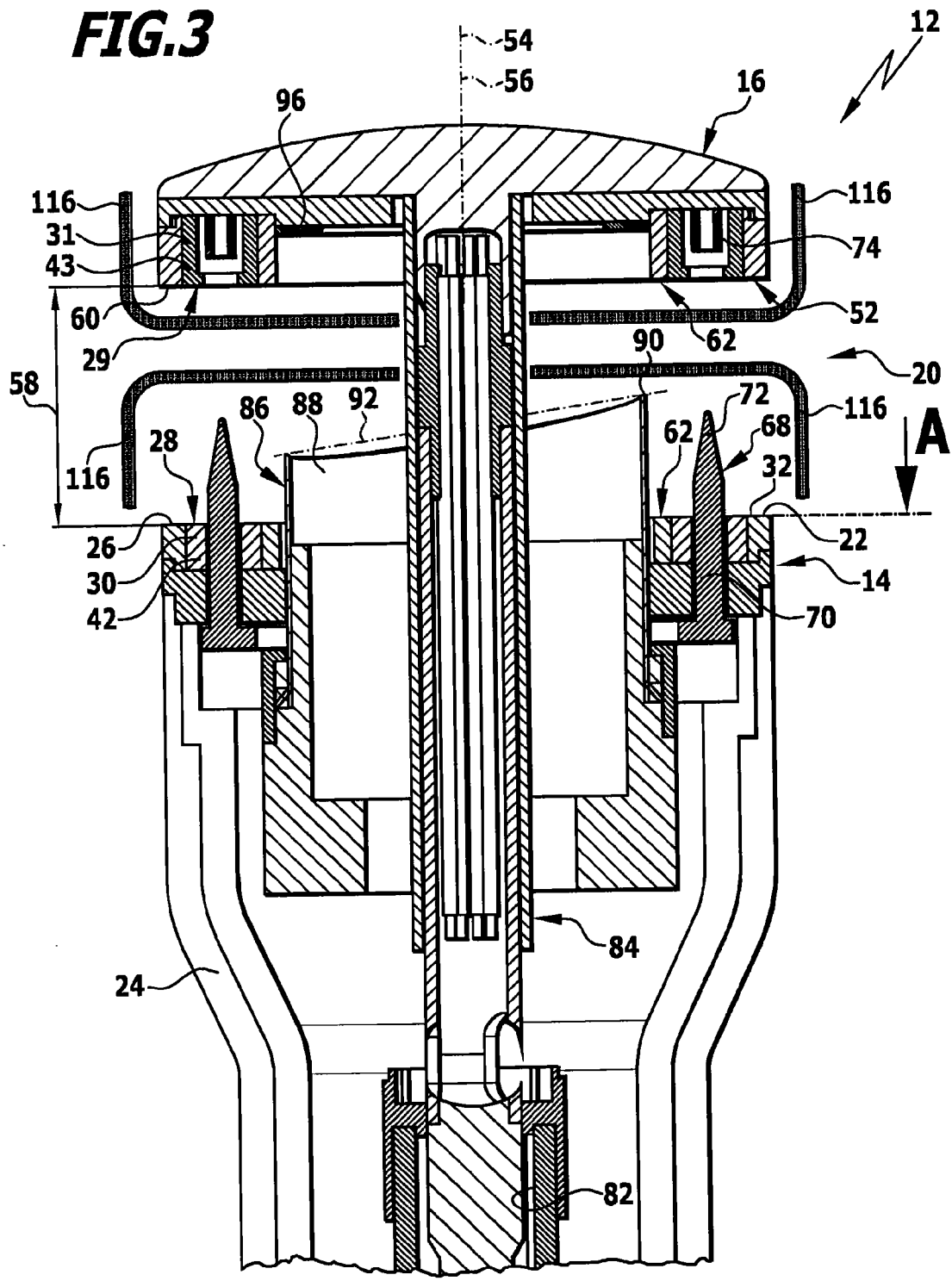
FIG. 3 shows a longitudinal sectional view of the instrument from FIG. 1 in area A before connecting two tubular tissues.

At its distal end, the force transmission member 80 defines a blind-hole-like mount 82, into which a holding member 84 with a first free end can be inserted and can then be fixed in the mount 82. The second free end of the essentially rod-shaped holding member 84 is immovably connected to the second tool element 16. In this way, as a result of a displacement of the force transmission member 80 in the distal direction, the second tool element 16 can be moved away from the first tool element 14. The instrument 12 is preferably designed, such that the second tool element 16 can be brought from a tissue gripping position, as it is schematically shown in FIGS. 2 and 3 and in which the tool elements 14, 16 have a maximum distance 58 from one another, into the position of proximity or the tissue connection position by pivoting the actuating members 78 towards one another, which results in a movement of the force transmission member 80 in the proximal direction.

Furthermore, the instrument comprises a cutting means 86 for cutting tissue. The cutting means 86 comprises a cutting element 88 with a self-contained circular cutting edge 90. The cutting edge 90 defines a cutting plane 92 sloped in relation to the longitudinal axis 54 of the instrument 12. The cutting plane 92 is sloped by approx. 10° in relation to a reference plane running at right angles to the longitudinal axis 54, which runs parallel to the tool element surfaces 32 and 33. On the proximal side, another RF cutting terminal 94, which in a variant of the instrument 12 is connected in an electrically conductive manner to the cutting element 88, is provided at the shaft 24. Thus, for example, a monopolar cutting means 86 can be implemented, whereby a neutral electrode would usually be applied for monopolar cutting at the body of the patient. A bipolar cutting means 86 is, for example, implemented by a ring electrode 96 being arranged opposite cutting edge 90 at the second tool element 16, which is connected to another RF cutting terminal 94 via an electrically conductive connection (which is not shown in detail), which runs, for example, through the force transmission member 80 in a manner not shown. The ring electrode 96 itself may also be selectively segmented, for example, similar to the RF electrodes 28 and 29. It would also be possible to use the RF electrode 29 as a counterelectrode instead of the ring electrode 96.

The cutting element 88 is preferably mounted displaceably in relation to the two tool elements 14, 16. The cutting edge 90, which is designed as concentric about the longitudinal axis 54, can thus be displaced in relation to the RF electrodes 28 and 29. For actuating the cutting means 86, a cutting actuating means 98 is provided with an actuating member 100 projecting from the proximal end of the instrument. This is mechanically coupled to the cutting element 88 via a mechanism (which is not shown), for example, another force transmission member running in the interior of the shaft 24, such that, as a result of a movement of the actuating member 100, the cutting element 88 is moved as well. The actuating member 100 is preferably arranged displaceably and rotatably in relation to the shaft 24, such that the cutting element 88 can be not only displaced parallel to the longitudinal axis 54, but also rotated in relation to same.

In order to be able to apply RF current to the electrode segments 30, 31 as desired, a control and/or regulating means 102 is provided with a switching means 104. The control and/or regulating means 102 is preferably arranged in a housing of the RF current generator and forms a part of same. The switching means 104 is especially designed for the sequential application of an RF current to the electrode segments 30, 31. The switching means 104 is especially used for controlling the contacts 66 as well as further contacts 106, which can be connected to the RF cutting terminals 94 of the instrument 12 via further connecting lines 108. In this way, the cutting means 86 can be operated in a monopolar or bipolar manner with the RF current generator 18. For the monopolar operation, RF current is applied only to the cutting element 88 and a neutral electrode is arranged at the body of the patient as a counterelectrode. For bipolar cutting, especially a circular counterelectrode may be provided at the second tool element 16, for example, in the form of the ring electrode 96, such that an RF current can then flow between the counterelectrode and cutting element 88. As an alternative, the RF electrode 29 may also be used as a counterelectrode. If a current feed of the cutting means 86 is entirely dispensed with, then this may also be used purely mechanically for cutting tissue and by means of the preferably sharpened cutting edge 90.

The switching means 104 may further also be designed such that RF current can be simultaneously applied to at least two electrode segments 30, 31 of an RF electrode 28, 29. It is advantageous here when another electrode segment 30, 31, which is then currentless, however, is arranged between two electrode segments 30, 31, to which RF current is applied simultaneously. For example, in this way the electrode segments 30 of the RF electrode 28 shown in FIG. 5 lying opposite one another might be fed current simultaneously, whereby the two other electrode segments 30 then remain currentless.

In order to be able to individually adjust a current feed intensity and/or a duration of current feed for the individual electrode segments 30, 31, the control and/or regulating means 102 is designed as comprising an adjusting means 110. By means of the adjusting means 110, for example, an intensity and/or a frequency of the RF current, just as a duration of current feed, can be adjusted. Moreover, the adjusting means 110 may optionally also be designed to be able to adjust current feed sequences individually.

Furthermore, the control and/or regulating means 102 preferably comprises a temperature measuring means 112 for measuring an electrode segment temperature and/or tissue temperature. Temperature measuring means 112 is especially used for supplying the control and/or regulating means 102 the controlled variables needed for an automatic regulation of a current feed of the RF electrodes 28, 29, especially a temperature of the tissue, for example, indirectly via a temperature measurement of the electrode segments 30, 31. For example, electrode segments 30, 31, which are not fed current, may be used as measuring contacts for determining the temperature via a measurement of the tissue impedance. In this way, it can be guaranteed that the temperature needed for connecting the tissue in a desired and highly precise manner is achieved by the corresponding feed of current to the RF electrodes 28, 29, but an undesired overheating of the tissues to be connected to one another is prevented.

Further, the control and/or regulating means 102 optionally comprises an impedance measuring means 113 for measuring a tissue impedance of tissue held between the tool elements 14 and 16. The determination of the tissue impedance makes it possible, depending on its value, to regulate the RF generator 18, especially the parameters of voltage, current or power provided by same. In this way, the energy to be introduced into same for connecting the tissues can be regulated in a simple and reliable manner. Especially the RF electrodes 28 and 29 can be used for measuring the tissue impedance. A measurement may also be performed between individual electrode segments 30 and 31, which lie opposite one another. The tissue impedance measurement may take place selectively during the current feed of RF electrodes 28, 29 or when RF electrodes 28, 29 are just currentless. Thus, the change in the tissues can be monitored well and practically in real time and further energy input can be metered, stopped or specifically further permitted.

With the surgical system 10 described above, especially tubular tissues 116 can be connected to one another directly by being welded or sealed to one another by means of RF current. In particular, the procedure is, for example, as follows:

For making an end-to-end anastomosis of two tubular tissues 116, as is necessary, for example, after a bowel surgery, in which a piece of the bowel is removed, free ends of the tissues 116 are brought towards one another, such that they lie against one another in a circular, flat manner, as shown, for example, in FIGS. 3 and 4, with their free ends pointing in the direction of the longitudinal axis. The free ends are then located between the two tool elements 14, 16, such that the tissues 116 can be held together, being gripped between the tool elements 14, 16 in the tissue gripping position.

The tool elements 14, 16 are then moved towards one another into the tissue connection position, such that the electrode segments 31 are also connected in an electrically conductive manner to the RF terminal contacts 50 in the manner described above. For welding the tissues 116, an RF current is now preferably applied to individual pairs of electrode segments 62, which then flows over the tissue sections held between the tool elements 14, 16 and heats same. At a temperature of approx. 50° C. to approx. 80° C., and preferably approx. 65° C. to approx. 70° C., a change takes places in the cells, such that the tissues 116 bond to one another. The connection process is preferably carried out such that always only one pair of electrode segments 62 is simultaneously fed current, especially in a sequential succession. In this way, a circular connecting line 114 is produced, which is essentially predetermined by the RF electrodes 28, 29 or their electrode center lines 44, 45.

The temperature can be much better controlled for connecting the tissues 116 and a destruction of the cells can be prevented by an RF current not being applied to all the RF electrodes 28, 29. The electrode segments 30, 31 are preferably fed current one after the other, i.e., sequentially, such that the tissues 116 are welded to one another in sections along the connecting line 114. Furthermore, a double connection between the tissues 116 is produced by the two-row arrangement of the electrode segment sections 38, 39, 40 and 41, which can guarantee an optimal sealing and a permanent, stable connection of the tissues 116 to one another.

As an alternative to a sequential current feed, as already indicated above, electrode segments 30, 31 lying opposite one another may also be fed current simultaneously, as a result of which the time for connecting the tissues 116 can be cut in half in the exemplary embodiment schematically shown in FIGS. 1 through 5.

After connecting the tissues 116, protruding tissue is removed by means of the cutting means 86. In this case, the cutting means 86 is preferably used in a bipolar mode, i.e., the cutting element 88 and the ring electrode 96 are connected to the RF current generator 18 and an RF current is conducted over the two tissues 116 to cut the tissue. Due to the sloped cutting edge 90, a defined cutting spark is produced, and precisely in the area in which the distance between the cutting edge 88 and the ring electrode 96 is minimal. Starting from this area, the cutting spark then travels automatically along the cutting edge 90 in both directions around in a circle until the tissue is completely severed. The use of the cutting means 86 in the bipolar mode of operation has especially the advantage that the tissues 116 are also simultaneously coagulated during the cutting in order to stop undesired bleeding directly during the cutting.

After connecting and cutting the tissues 116, the instrument 12 can then be withdrawn from the body of the patient, for example, from his/her bowel, by withdrawing the shaft 24.

Depending on the embodiment of the instrument 12, the shaft 24 is preferably so long that both the actuating means 76 and the cutting actuating means 98 still protrude from the body of the patient during the use of the instrument 12, so that they can be actuated by a surgeon.

Figure 6:
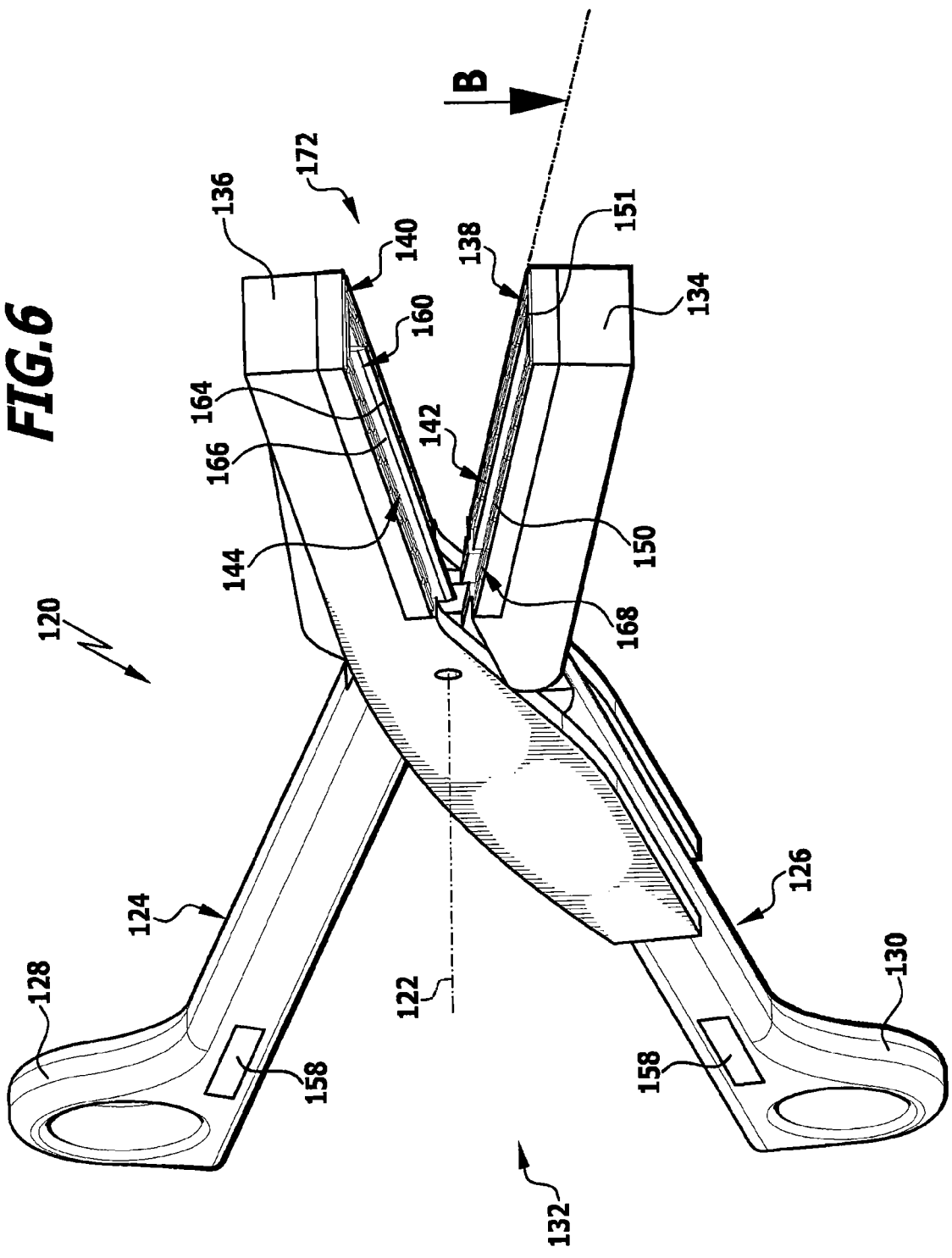
FIG. 6 shows a perspective, schematic view of a second exemplary embodiment of a surgical instrument for connecting body tissues.
Figure 7:
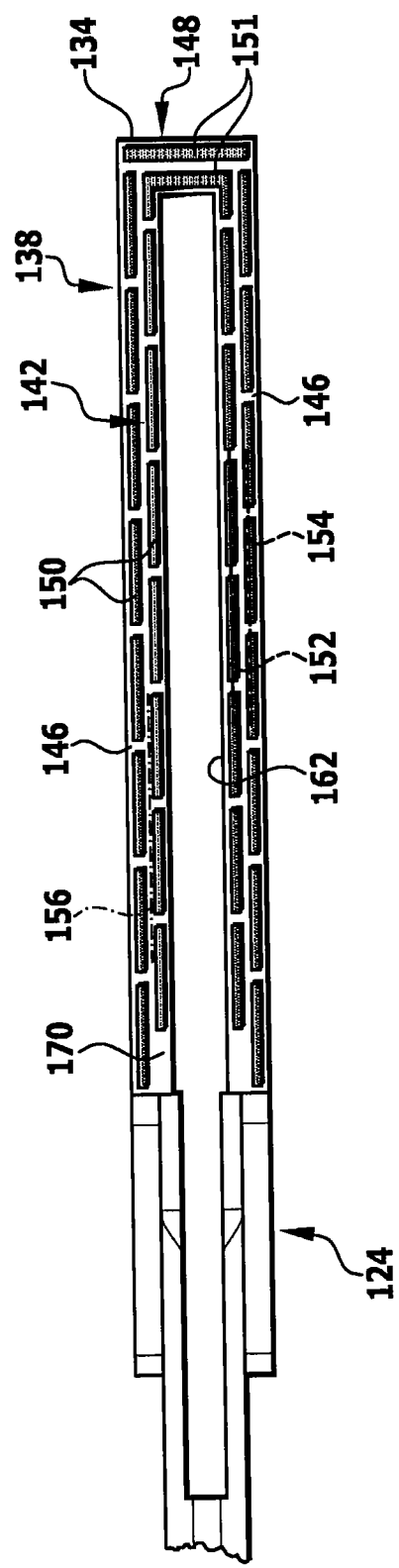
FIG. 7 shows a top view of a schematically shown tool element surface of the instrument from FIG. 6 in the direction of arrow B.

As an alternative or in addition, the surgical system 10 may comprise, instead of the instrument 12, also a surgical instrument, for example, in the form of an instrument 120 schematically shown in FIGS. 6 and 7. The instrument 120 comprises two branches 124 and 126 mounted on one another pivotable in relation to one another about a pivot axis 122. Finger rings 128, 130, which together define an actuating means 132 for actuating the instrument 120, are formed at a proximal end of the branches 124, 126.

Starting from free, distal ends 134 and 136 of the branches 124 and 126 are formed tool elements 138 and 140 pointing towards one another on the insides of same. The tool elements 138 and 140 have an identical design and lie opposite one another in a position of proximity of the ends 134 and 136 and have a minimal distance from one another in this position. Each tool element 138, 140 comprises an RF electrode 142, 144, which have an identical and essentially U-shaped design. Each RF electrode 142, 144 comprises two electrode sections 146, running parallel to one another and extending in a direction at right angles to the pivot axis 122, as well as an electrode section 148 running at right angles to same, adjacent to the ends 134, 136.

The structure of the RF electrodes 142, 144 is described in detail below, for example, in connection with FIG. 7 based on the RF electrode 142.

RF electrode 142 comprises a total of 30 electrode segments 150, whereby 15 electrode segments each are arranged offset to one another in two rows of electrodes 152, 154 parallel to one another along each electrode section 146 and electrically insulated from each other. The electrode segments 150 have a linear and strip-shaped design. They define between them an electrode center line 156, which likewise has a U-shaped design corresponding to the shape of the RF electrode 142. Two other electrode segments 151, which complete the rows of electrodes 152 or 154 of the electrode sections 146, respectively, are arranged in the area of the electrode section 148. Thus, the electrode segments 150 and 151 are arranged offset to one another in a direction defined by the electrode center line 156.

To be able to apply an RF current to the electrode segments 150, 151, these are each arranged in an electrically conductive manner with an RF terminal 158 in proximal end areas of the branches 124, 126 adjacent to the finger rings 128, 130. The RF terminals 158 can be connected to the RF current generator 18 with corresponding connecting lines or cables.

Because of the identical design of the RF electrodes 142 and 144, electrode segments 150 and 151 which are the same size or essentially the same size lie opposite one another and point towards one another in the position of proximity. They form a pair of electrode segments, which is designated as a whole with the reference number 168. Thus, the instrument 120 comprises a total of 32 pairs of electrode segments 168.

The tool elements 138 and 140 also define flat tool element surfaces 170, which have a U-shaped design. The electrode segments 150 and 151 do not protrude over the tool element surface 170.

The instrument 120, which has an overall tong-shaped design, may likewise be used for connecting tissues, whereby these are held gripped between the tool elements 138, 140 and then are welded or sealed to one another by means of corresponding application of current to the electrode segments 150, 151. As in connection with the function of the instrument 12 described, a current feed of the electrode segments 150 may be carried out sequentially for this, i.e., circulating in a U-shaped manner, after feeding an electrode segment 150 with current, the nearest electrode segment 150 of the adjacent row of electrodes 152, 154 is fed current until all electrode segments 150, 151 were fed current once. In this way, a two-row connecting line for connecting two tissues can be produced. As an alternative, a simultaneous current feed of two or even more electrode segments 150, 151 is also conceivable in the instrument 120, whereby electrode segments 150, 151, which are adjacent to one another, are preferably not fed current simultaneously, but rather preferably at least one, preferably two or three electrode segments 150, 151 remain currentless between electrode segments 150, 151 that are fed current simultaneously.

The instrument 120 may optionally also comprise a cutting means 160, as it is schematically shown in FIG. 6. A slot 162 each is formed between the electrode sections 146 at the tool elements 138, 140. A cutting element 164 with the cutting edge 166 pointing in the direction of the slot 162 of the branch 124 is held and can optionally be moved in relation to the tool element 136 in the slot 162 of the branch 126. Thus, for example, the tissue held between the tool elements 138 and 140 can be cut already when the branches 124 and 126 are closed. Optionally, the cutting element 164 may also be used in monopolar or bipolar mode, whereby, for example, the RF electrode 142 can be used as a counterelectrode to the cutting element 164 in bipolar mode. For the monopolar operation, an RF current is applied only to the cutting element 164 and a neutral electrode is then arranged as a counterelectrode at the body of the patient. In both cases, the cutting element 164 is preferably also connected in an electrically conductive manner to a contact of the RF terminals 158.

FIGS. 8 through 11 show a variant of the instrument 12 which is distinguished by the design of the second tool element which is designated with reference number 16' in FIGS. 8 through 11. Tool element 16' adopts a circular ring shape in an operating position, in which it can be brought into the position of proximity described above. It comprises two circular ring sections 180 and 182, which extend each over an angle of approx. 180° in relation to the longitudinal axis 54. Free ends of the circular ring sections 180, 182 are only half as wide as the circular ring sections 180, 182 in the remaining area and are used as bearing blocks 184 and 186. Bearing blocks 184 and 186 are each provided with a cross hole 188 and 190, into which a cylindrical rod 192 is inserted. Bearing blocks 184 lie against bearing blocks 186 on their side facing the longitudinal axis 54. The rod 192 is fixed adapted to rotate in unison in the cross holes 190 of the circular ring section 182. The cross hole 188 is dimensioned in its inside diameter such that the circular ring section 180 is pivotable in relation to the rod 192 about a pivot axis 242 defined by same and thus in relation to the circular ring section 182.

The two circular ring sections 180 and 182 are each additionally coupled via rod-shaped connecting rod 194 with a holding member 84', which defines a holding member longitudinal axis coinciding with the longitudinal axis 54. The holding member 84', similar to holding member 84, is coupled or can be coupled with the force transmission member 80, and in this way can be moved in relation to the shaft 24 in the distal and proximal direction. For the movable articulation of the connecting rod 194 at holding member 84', the latter is provided in the area of its distal end with a slot 204, which extends transversely to a longitudinal axis defined by the rod 192. In this way, two legs 206 are formed, which are provided with an aligning cross hole 208, into which a cylindrical mounting pin 210 is inserted adapted to rotate in unison. The connecting rods 194 are provided at their first ends with a mounting hole 212, through which the mounting pin 210 extends and which has an inside diameter to make possible a pivoting movement of connecting rods 194 about a pivot axis defined by the mounting pin 210.

Approximately on the proximal side of the slot 204, a longitudinal slot or slotted hole 214, which is passed through by the rod 192, extends in the holding member 84' further in the proximal direction. In this way, the rod 192 is defined and is displaceable parallel to itself in a direction parallel to the longitudinal axis 54. A proximal end of the slotted hole 214 forms a proximal end stop for the rod 192, a distal end 218 of the slotted hole 214 forms a distal end stop for the rod 192.

An actuating mechanism 222, which comprises a sleeve-like force transmission element 220, whose inside diameter is adapted to the outside diameter of holding member 84' and thus is displaceable on holding member 84' in the distal and proximal direction, is used to move the rod 192. The force transmission element 220 is, adjacent to its distal end 224, provided with a hole 226, which the rod 192 passes through. The rod 192 is rotatable in relation to the hole 226. The actuating mechanism 222 can further form a part of the actuating mechanism 76 described above. This means that a movement of the rod 192 is possible, for example, even by a pivoting of the actuating members 100 in relation to one another. As an alternative, it would be conceivable to provide another actuating means similar to actuating mechanism 76, which comprises one or two other actuating members, similar to the actuating members 100, to implement specifically a relative movement between the force transmission element 220 and the holding member 84'.

On the top sides of the circular ring sections 180 and 182 are arranged two bearing blocks 228 each, which are parallel to one another and which, parallel to the cross hole 208, are provided with holes 230. Between the bearing blocks 228, another free end of the connecting rod 194 each is pivotably mounted on the bearing shaft 200 inserted in the holes 230. Due to the described arrangement of the connecting rods 194, which may also be designated as articulating members, it is guaranteed that with one end at the second tool element 16', they act on a point of action or hinge point, which is spaced away from the pivot axis 242.

Figure 8:
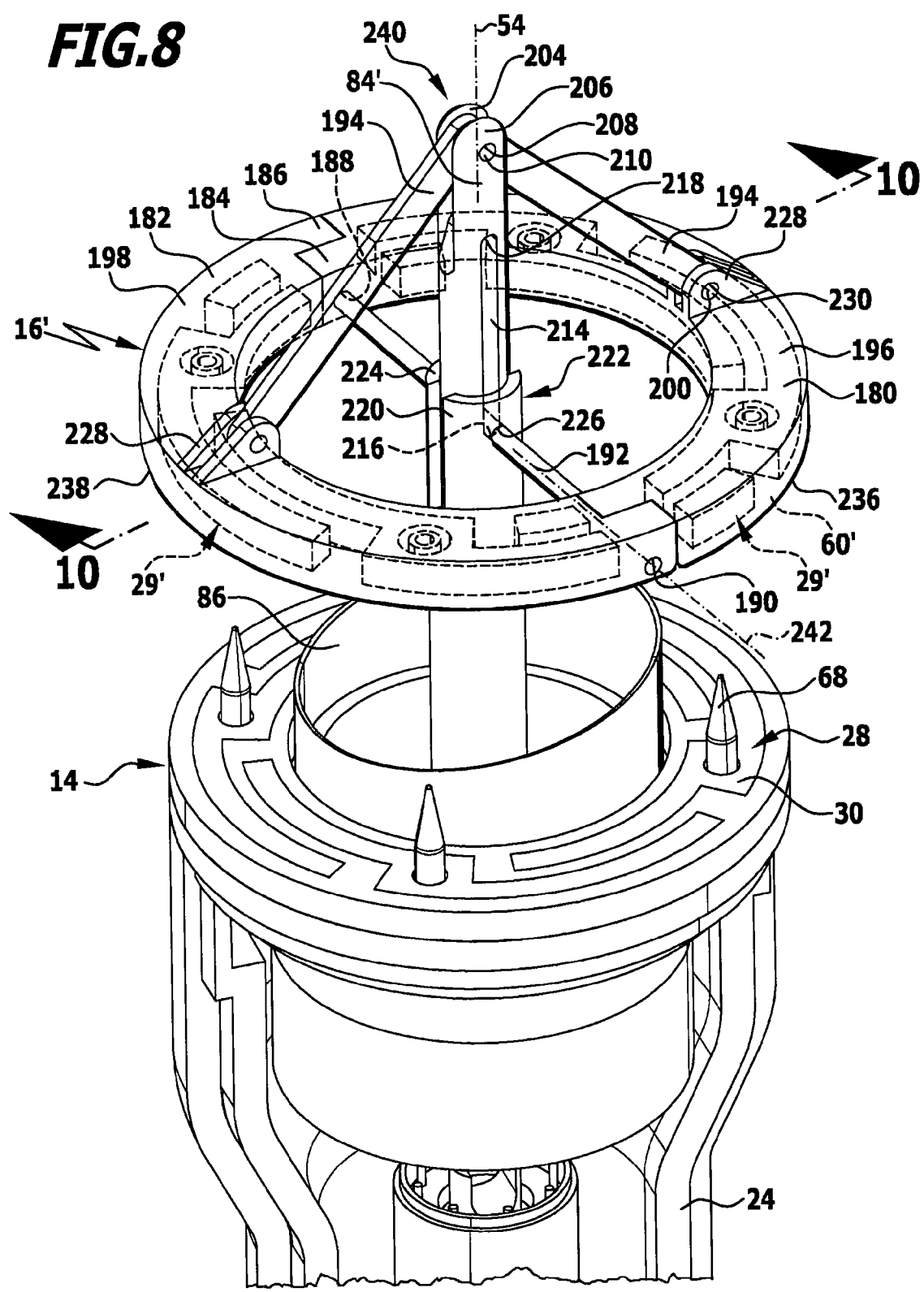
FIG. 8 shows a schematic view similar to FIG. 2 of an alternative embodiment of the instrument in a tissue gripping position.
Figure 9:
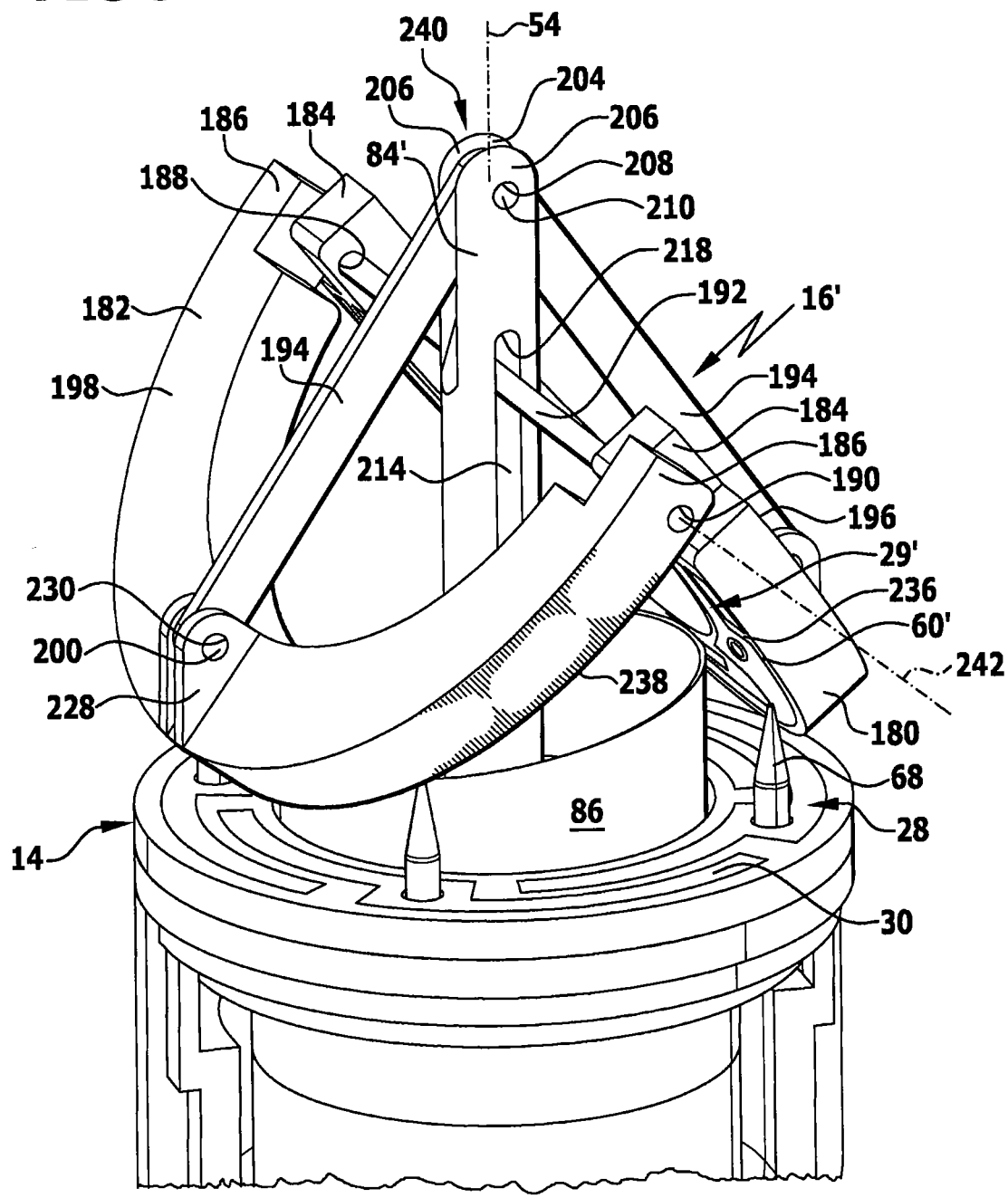
FIG. 9 shows a view corresponding to FIG. 8 of the instrument shown there with partly unfolded second tool element.
Figure 10:
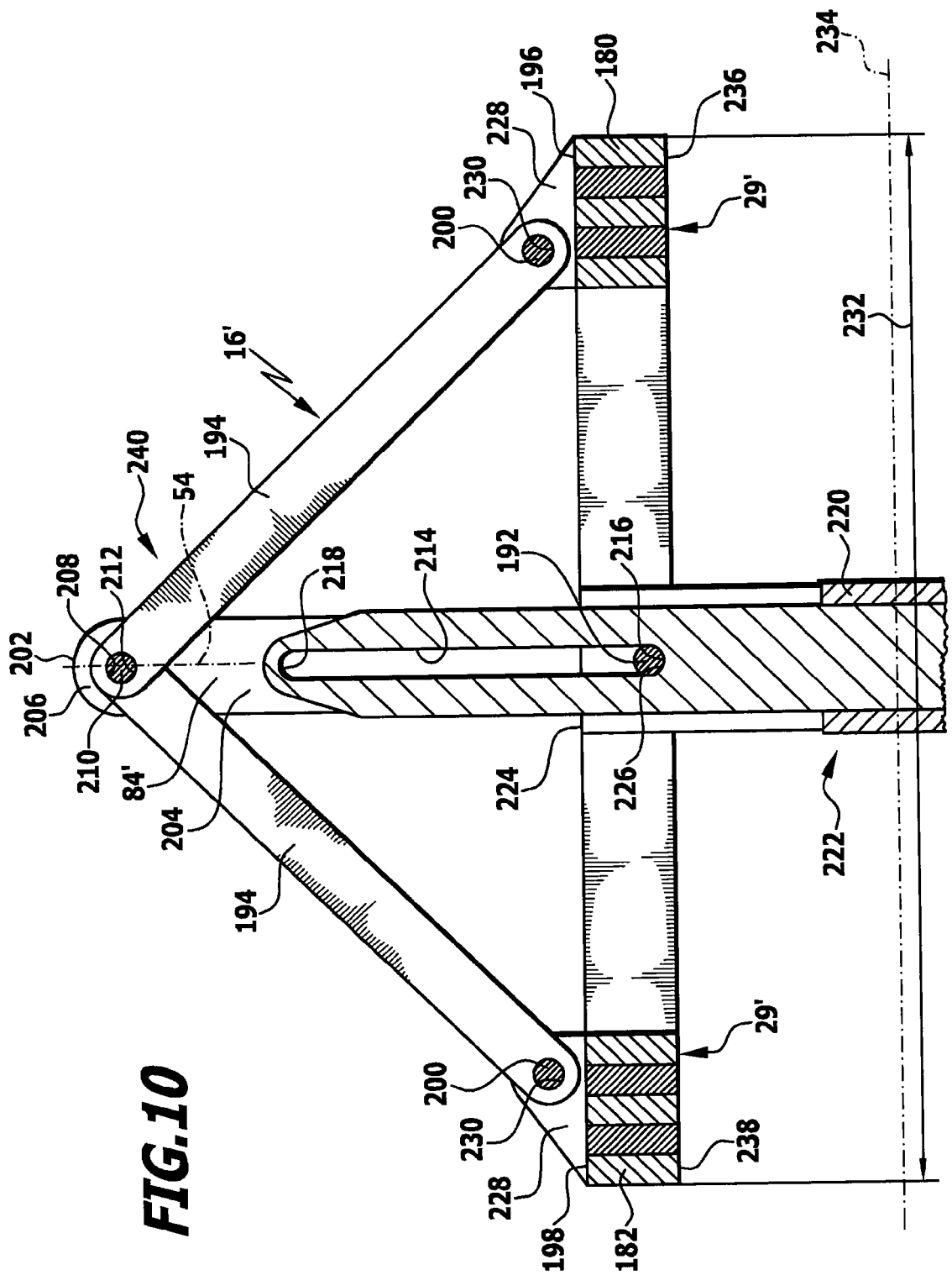
FIG. 10 shows a sectional view along line 10-10 in FIG. 8.
Figure 11:
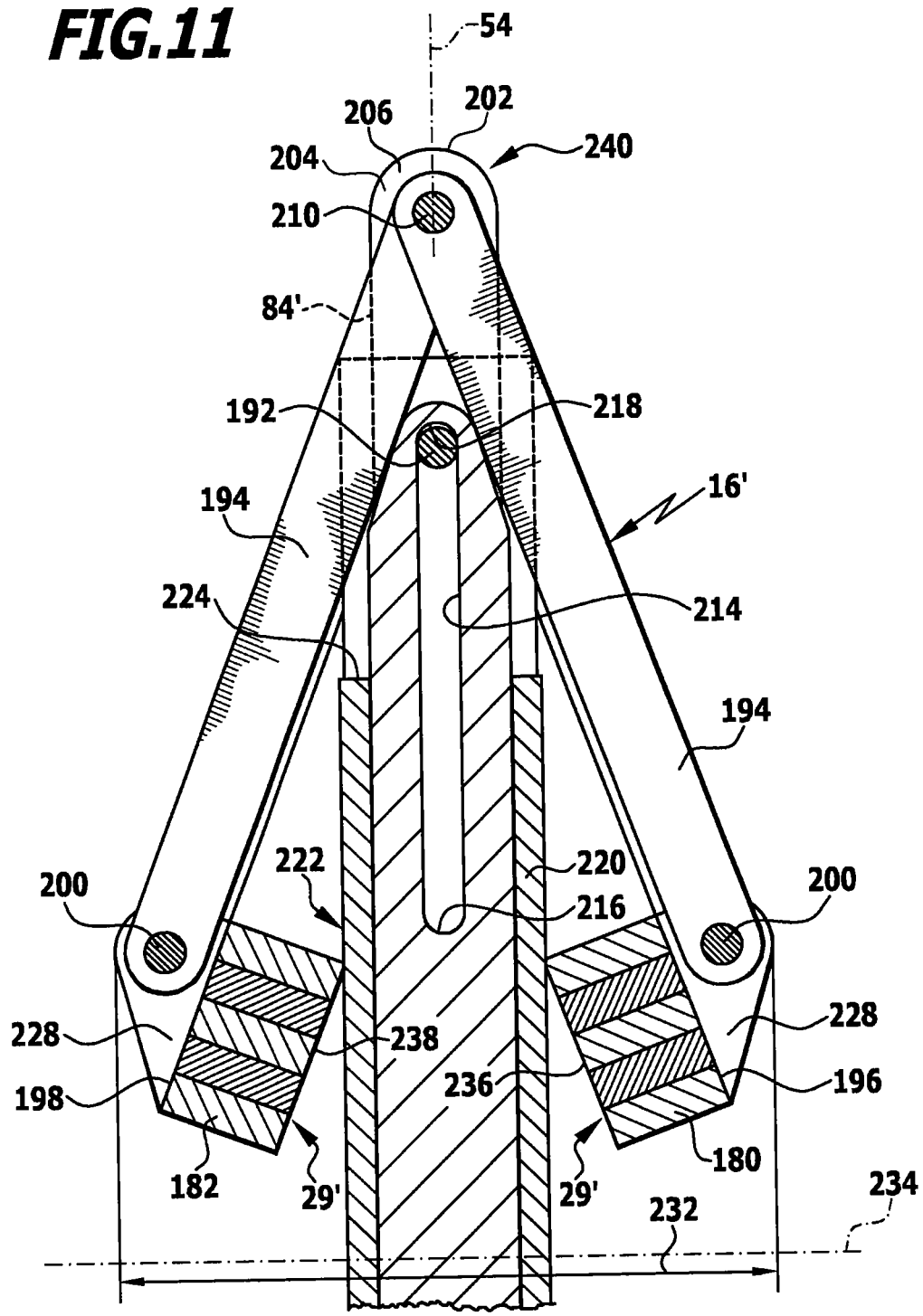
FIG. 11 shows a schematic sectional view similar to FIG. 10 of the second tool element folded up in a position as shown in FIG. 9.
Figure 12:
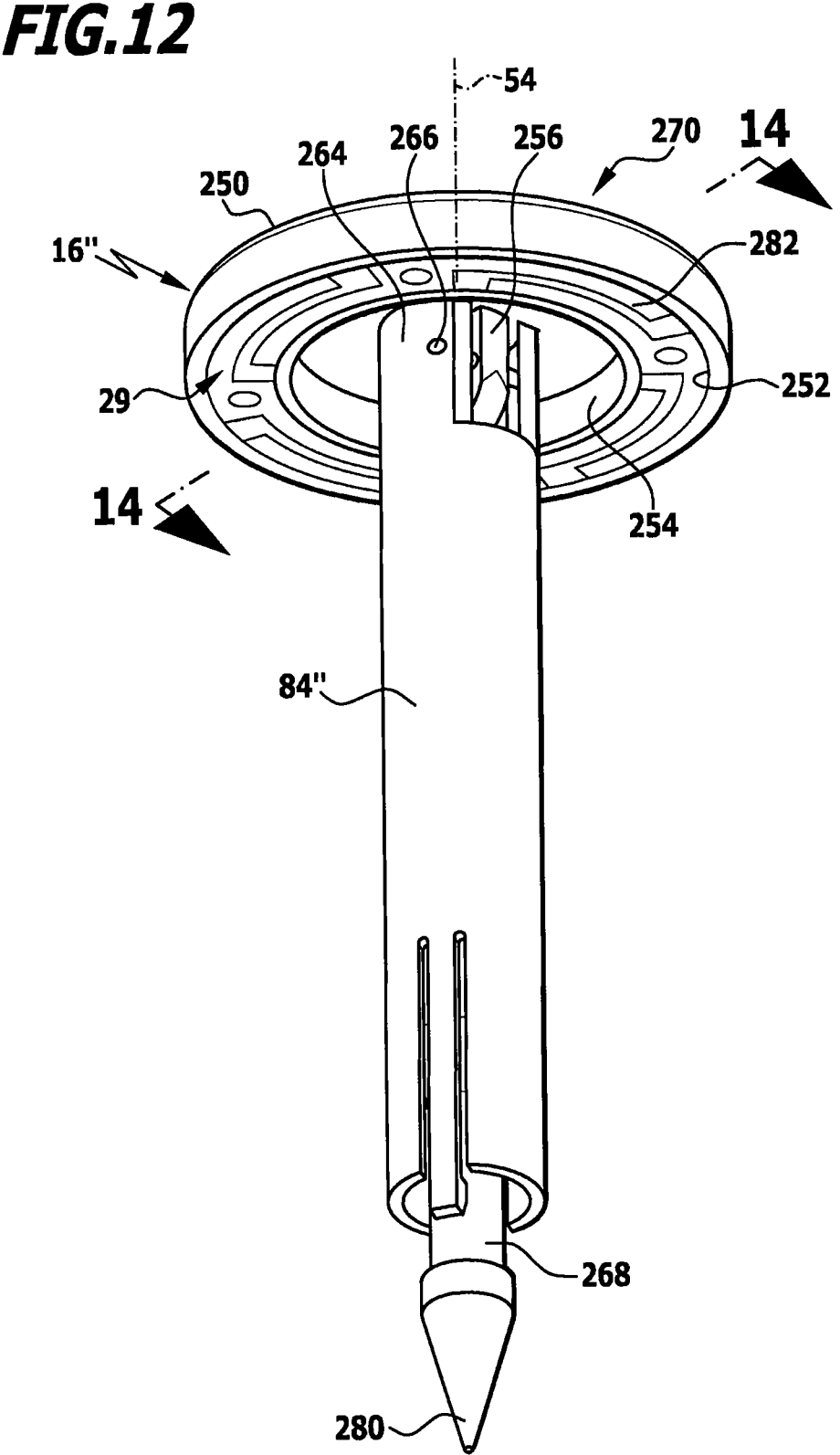
FIG. 12 shows a perspective schematic view of an alternative embodiment of a second tool element.
Figure 13:
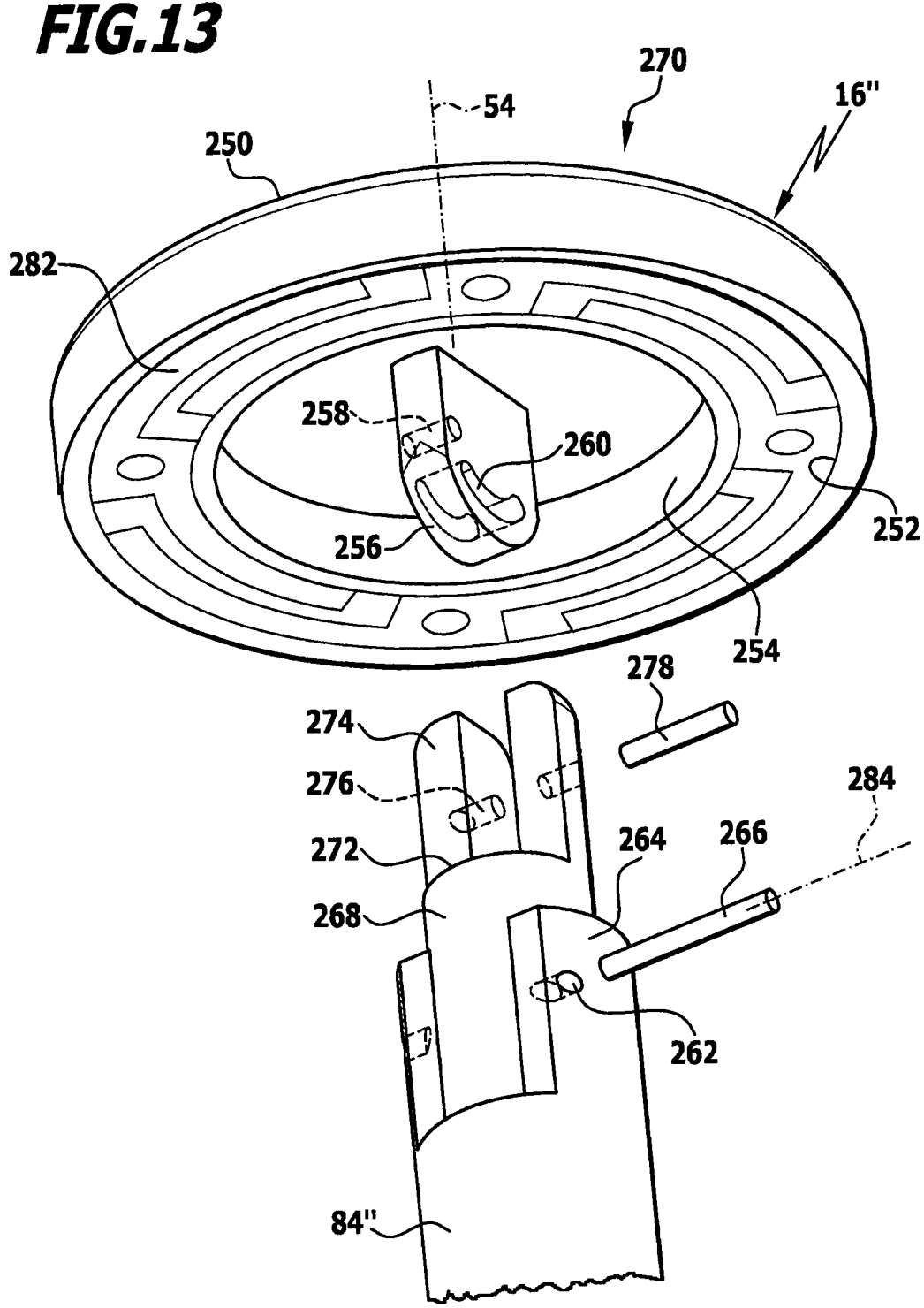
FIG. 13 shows an exploded view of a part of the second tool element shown in FIG. 12.

Using the actuating mechanism 222, the second tool element 16' can be brought from the operating position already mentioned, which is schematically shown in FIGS. 8 and 10, into the removal position, which is shown, for example, in FIG. 11. FIG. 9 schematically shows an intermediate position, i.e., a position between the operating position and the removal position. As can be easily seen by a comparison of the two FIGS. 10 and 11, a surface area of a vertical projection of the second tool element 16' is on a projection plane 234, which runs at right angles to the longitudinal axis 54, i.e., to the shaft direction in the area of second tool element 16', is smaller in the removal position than in the operating position. This is achieved by a movement of the sleeve-like force transmission element 220 starting from the operating position, in which the rod 192 stops at the proximal end 216 and bottom sides 236 and 238 of the circular ring sections 180 and 182 extend parallel to the projection plane 234. If the force transmission element 220 is moved in the distal direction, the rod 192 is forcibly guided in the slotted hole 214 in the distal direction. Due to the articulated connection of the circular ring sections 180 and 182 in relation to one another and via the two connecting rods 194 with the holding member 84', the circular ring sections 180 and 182 pivot about the pivot axis 242 in the direction of the longitudinal axis 54. The second tool element 16' is in this way folded together or folded up. Thus, due to the articulated arrangement of the circular ring sections 180 and 182 by means of the connecting rods 194, a folding mechanism 240 is formed for transferring the second tool element 16' from the operating position into the removal position.

The design of the bottom sides 236 and 238 of the second tool element has not been mentioned up to now. This may have either a single, essentially continuous ring electrode, which forms a single counterelectrode to RF electrode 28 of the first tool element 14. As an alternative, an RF electrode with two or more electrode segments 31, preferably corresponding to RF electrode 29, may also be formed on the bottom sides 236 and 238 similar to RF electrode 29. This then makes possible a connecting of tissues 116 in the operating position in the manner described above.

After connecting the tissues, the folding mechanism 240 can then be actuated, for example, by the corresponding actuating of the described actuating mechanism 222, as a result of which the holding member 84' is moved in the distal direction. If the force transmission element 220 is, for example, arranged fixed in relation to the shaft 24, then the second tool element 16' can be automatically folded up by a movement in the distal direction of the force transmission member 80. Due to the markedly reduced area requirement in the removal position, the second tool element can be guided through a connecting site formed by the connecting of the tissues 116 during the removal of the instrument 12, and without expanding the connecting site, which is markedly more sparing then guiding the second tool element through the connecting site in the operating position.

It goes without saying that electrically conductive connections of electrode 29 to the RF terminal contacts 50 can be routed, for example, via the connecting rods 94 and the holding member 84' to the RF terminal contacts 50 in the proximal end area of the shaft 24.

Another variant of a second tool element is designated as a whole with the reference number 16" in FIGS. 12 through 15. It replaces, for example, the above-described tool elements 16 and 16' of the instrument 12.

The second tool element 16" has an essentially plate-like design with a slightly convex, curved outside 250 pointing in the distal direction.

A ring groove 252, which is open pointing in the proximal direction, is formed on the bottom side of the second tool element 16". In the center is formed an essentially circular recess 252, in which an essentially cuboid bearing projection is arranged, which is designed as projecting coaxially to the longitudinal axis 54 in the proximal direction from the bottom side of second tool element 16". The bearing projection 256 is provided with a cross hole 258, which runs skew in relation to longitudinal axis 54. Furthermore, a curved guide slot 260, which is curved convexly pointing in the proximal direction, is formed at the bearing projection 256. A proximal end of the bearing projection 256 has a rounded outer contour.

The second tool element 16" is pivotably mounted on a sleeve-like holding member 84". For this purpose, the holding member 84" is provided with a cross hole 262, which passes through a wall 264 of the holding member 84" at two sites. A mounting pin 266 adapted to rotate in unison is inserted into the cross hole 262. It simultaneously passes through the cross hole 258 such that the bearing projection 256 is pivotable about a pivot axis 284 defined by the mounting pin 266. To be able to actuate a folding mechanism 270 provided also with the second tool element 16", a force transmission element 268 is provided, which has an essentially rod-shaped design and the holding member 84" passes through coaxially to the longitudinal axis 54. From an end surface 272 on the distal side of the force transmission element 268, two bearing journals 274 are arranged parallel to one another and projecting pointing in the distal direction, which are each passed through by an aligning hole 276. Another mounting pin 278, which is oriented parallel to the mounting pin 266, is inserted adapted to rotate in unison into the holes 276. An outside diameter of the mounting pin 278 is dimensioned such that it can pass through the guide slot 260 and can be moved in relation to same.

A proximal end 280 of the force transmission element 268 can preferably be coupled with the force transmission member 80, such that the second tool element 16" can also be moved as a result of a movement of same.

A circular electrode element 282, which preferably comprises an RF electrode 29 in the manner as described above, which is not shown in detail in FIGS. 12 through 15 for the sake of clarity, is inserted into the ring groove 252. As an alternative, a simple, continuous ring electrode may also be formed at the electrode element 282.

Figure 14:
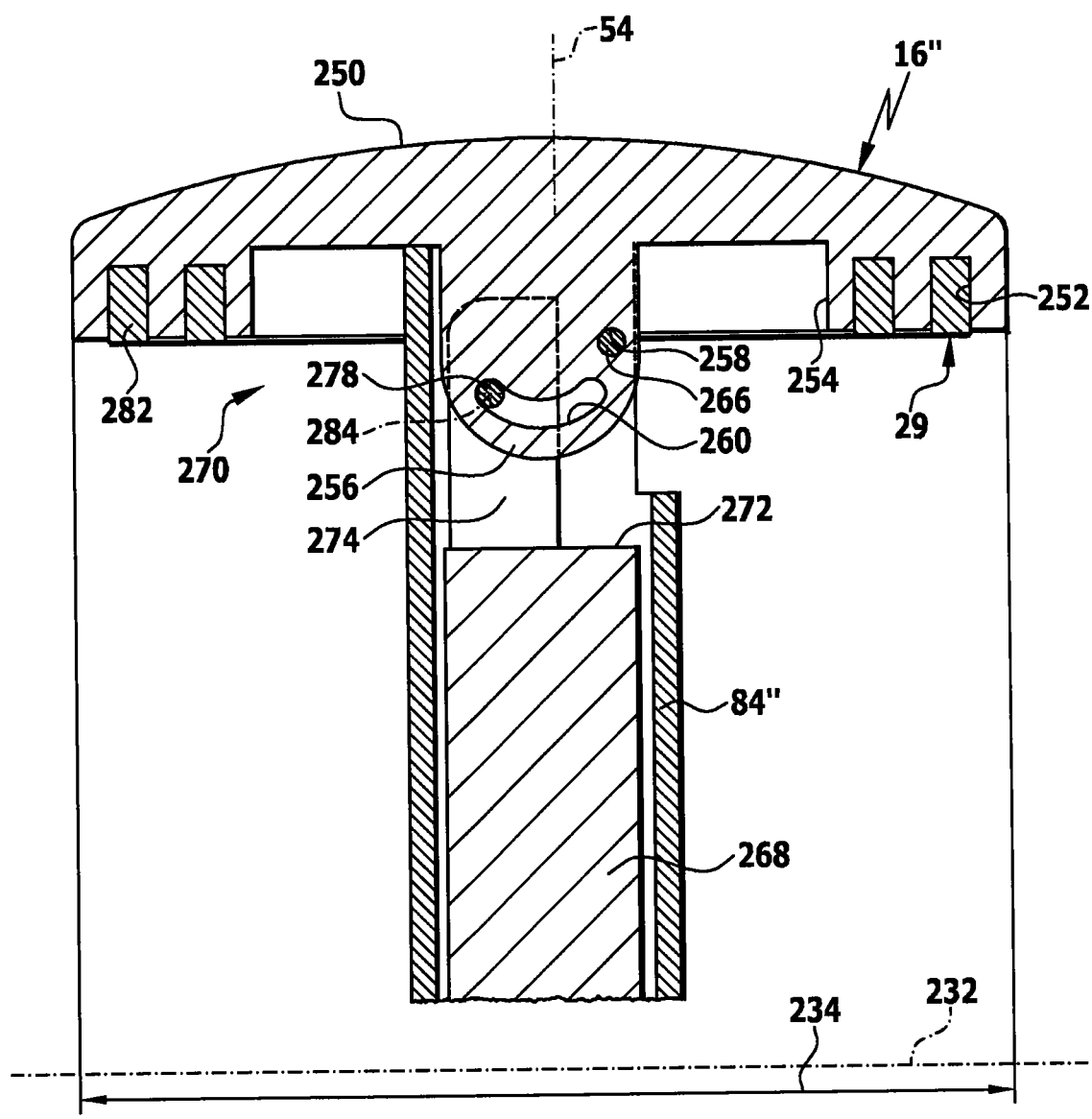
FIG. 14 shows a sectional view along line 14-14 in FIG. 12.
Figure 15:
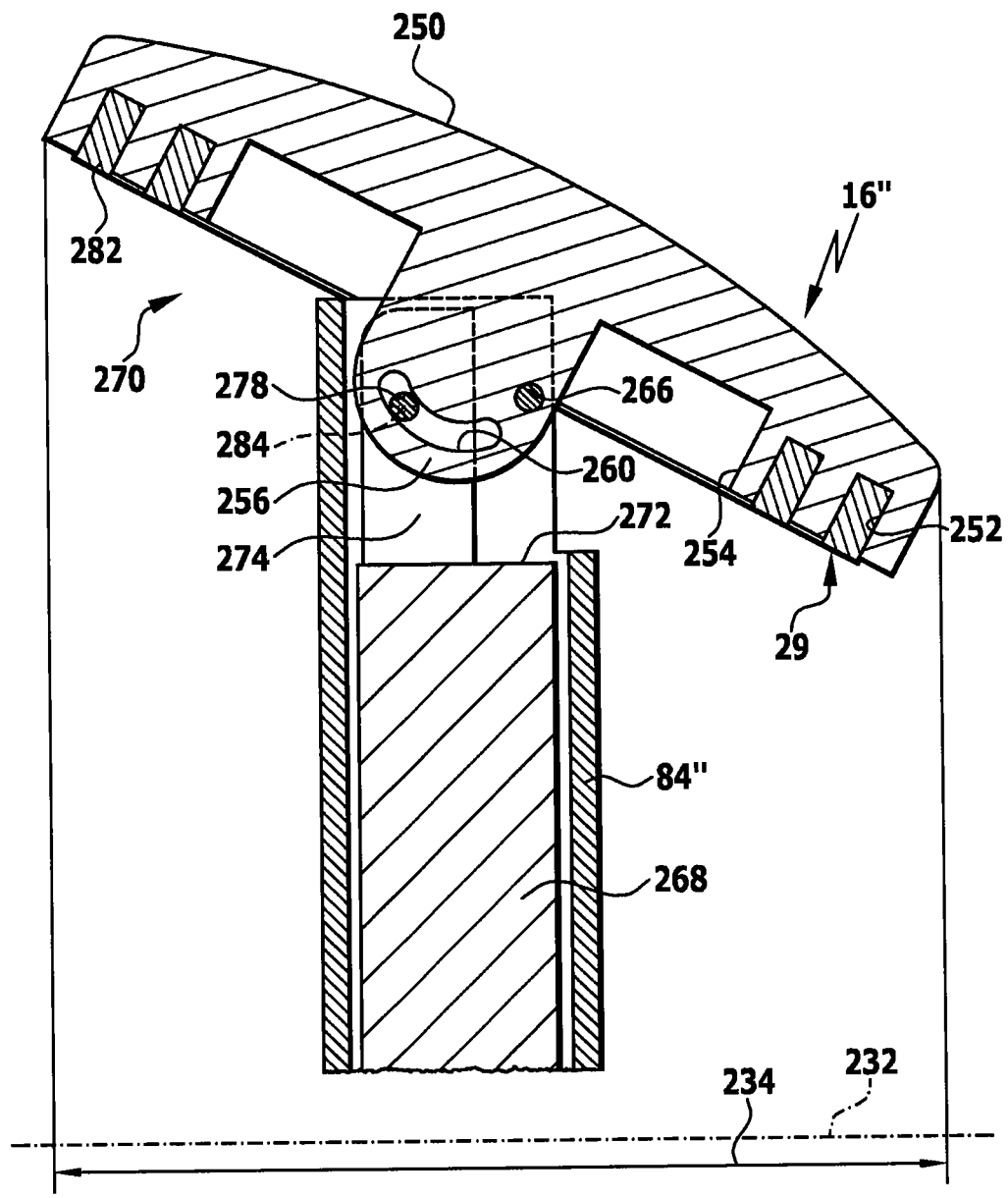
FIG. 15 shows a schematic sectional view similar to FIG. 14 of the exemplary embodiment shown there with partly unfolded second tool element.
Figure 16:
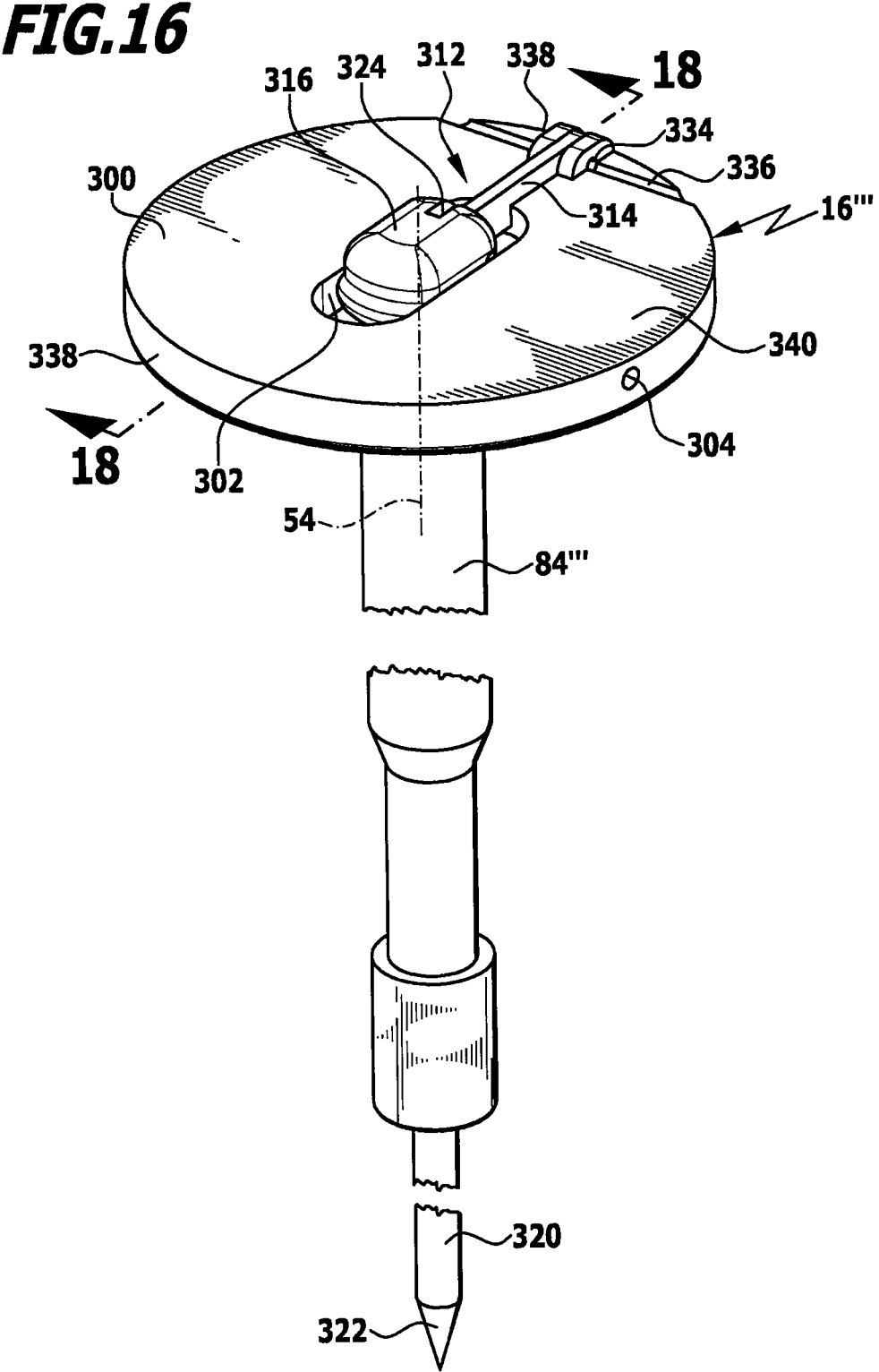
FIG. 16 shows a perspective schematic view similar to FIG. 12 of another exemplary embodiment of a second tool element.
Figure 17:
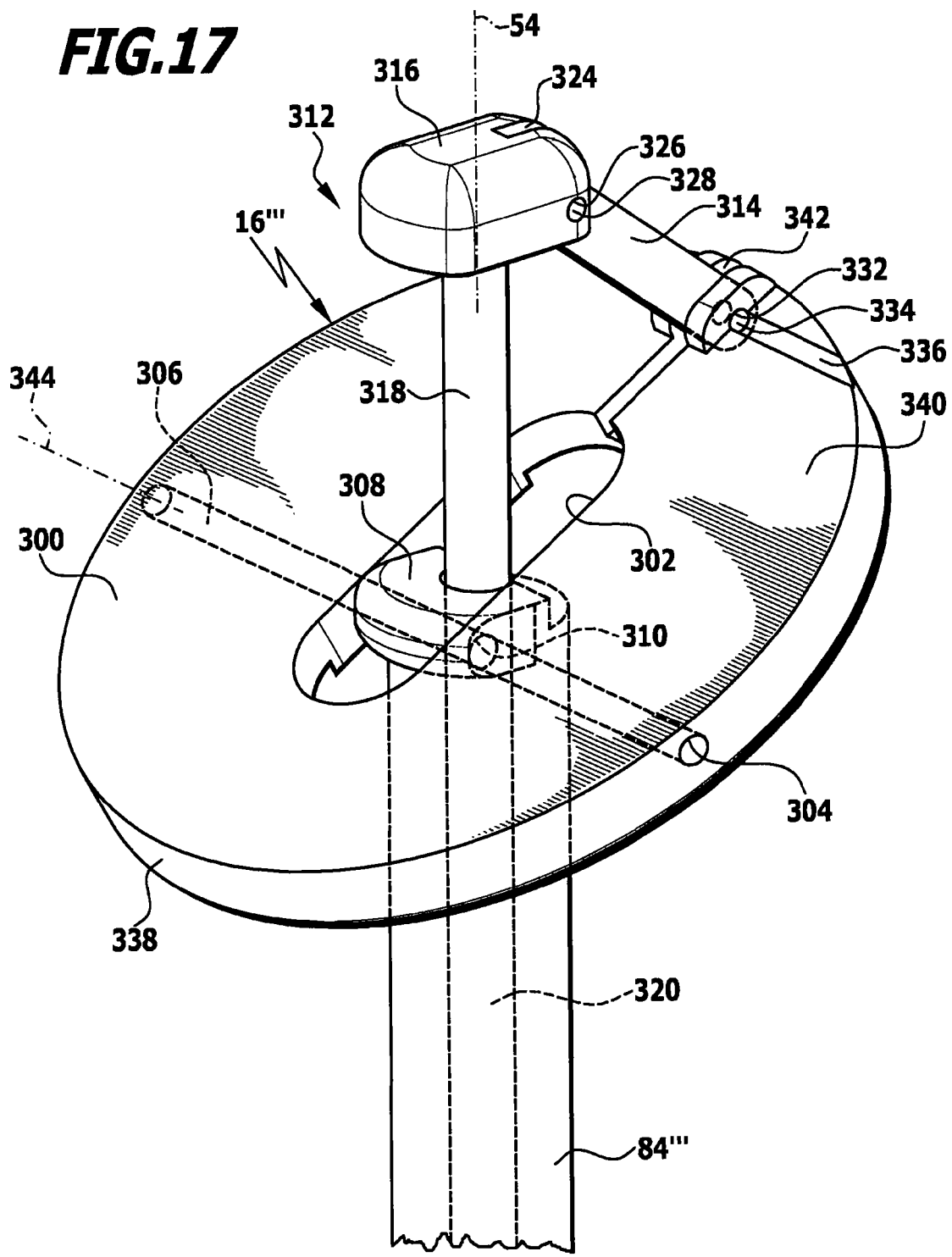
FIG. 17 shows an enlarged view of the second tool element from FIG. 16 in a partly sloped position.
Figure 18:
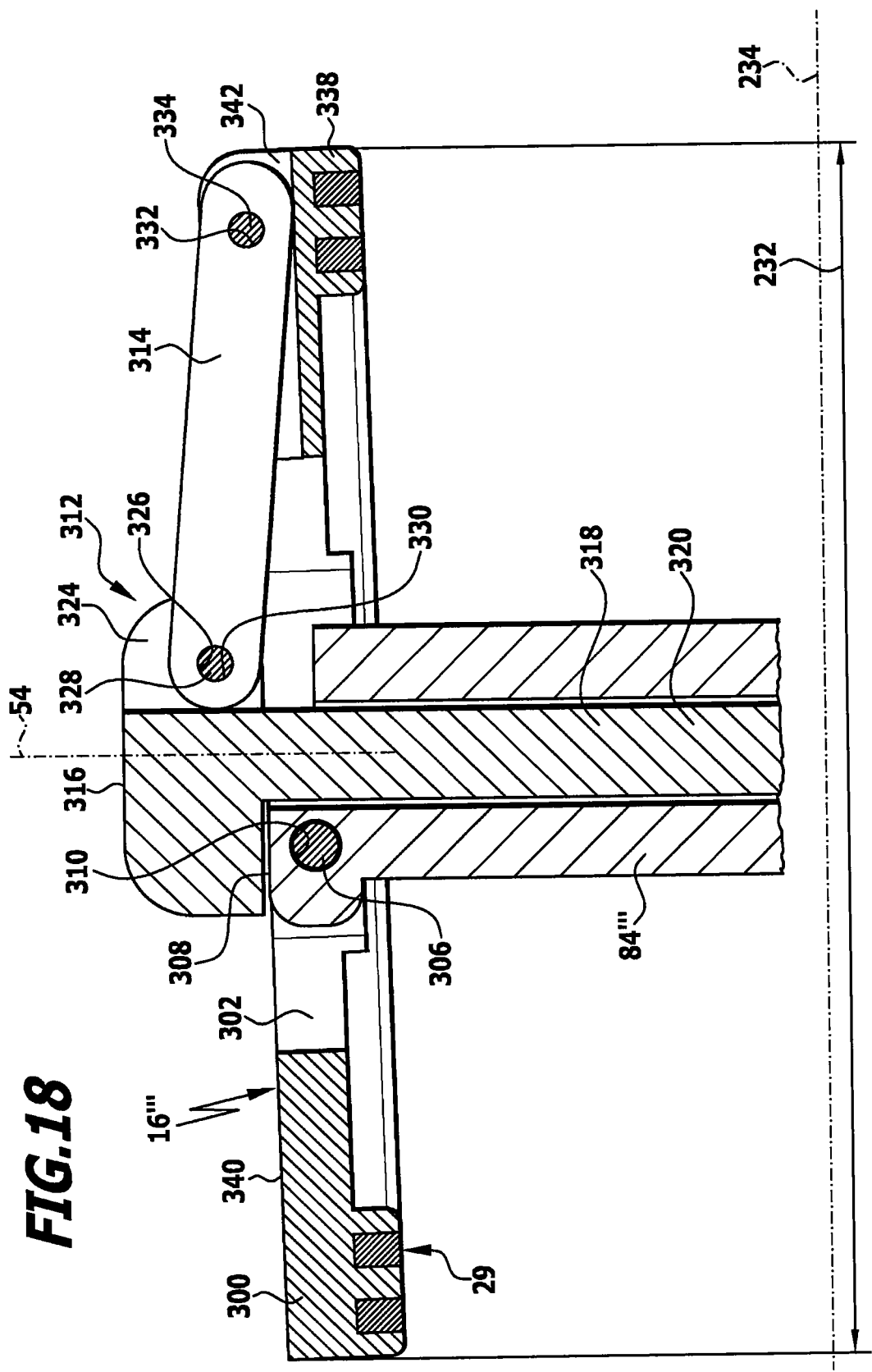
FIG. 18 shows a sectional view along line 18-18 in FIG. 16.
Figure 19:
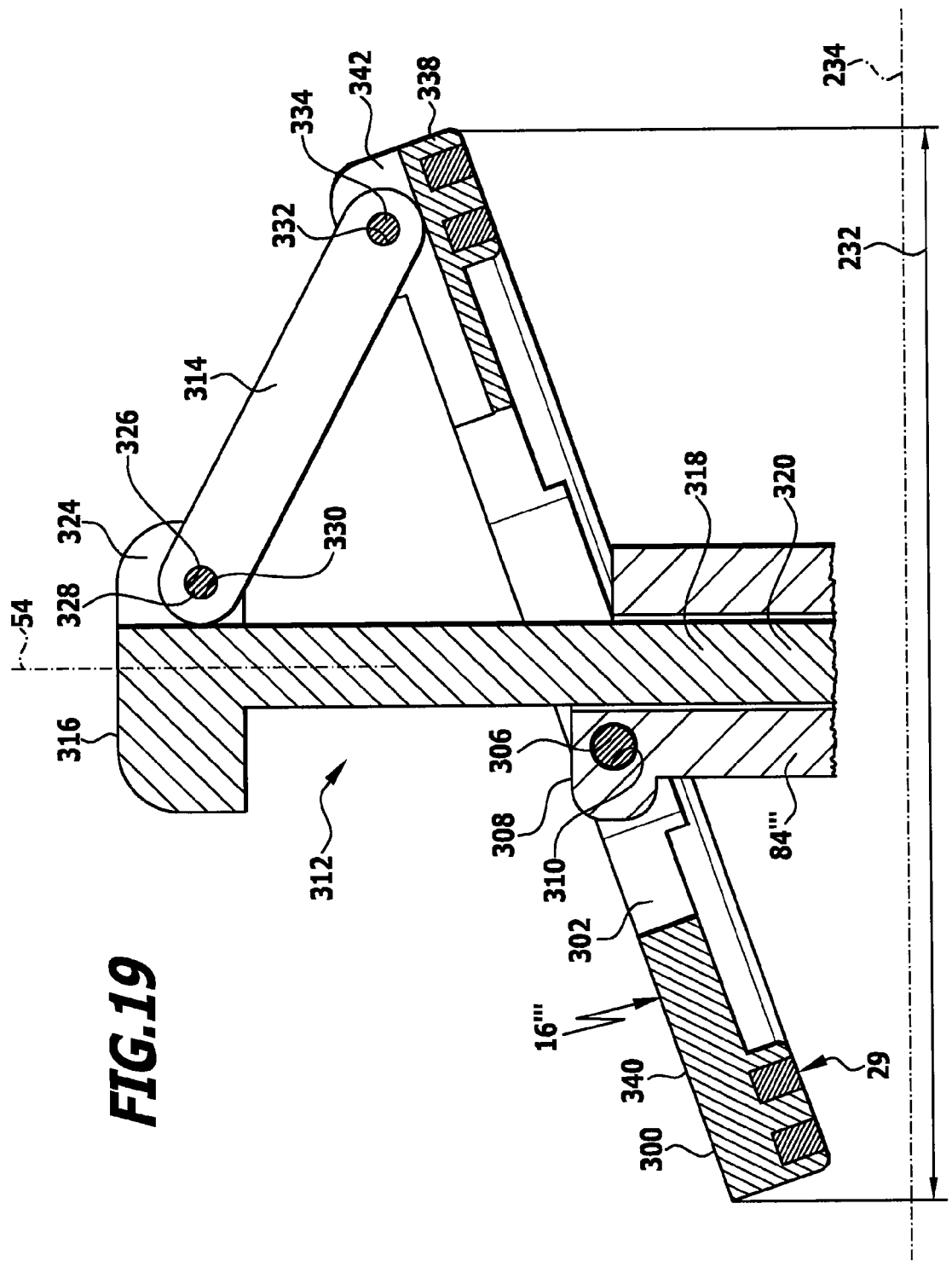
FIG. 19 shows a view similar to FIG. 18 with partly sloped second tool element in a position, as it is shown in FIG. 17.

For transferring the second tool element 16" from the operating position into the removal position, the force transmission element 268 is moved in the distal direction. Because of the specially curved guide slot 260, the mounting pin 278 is forcibly guided in same and thus brings about a forcibly guided pivoting of the second tool element 16" about the pivot axis 284. Essentially, the second tool element 16" can be pivoted about almost 90°, such that in this variant of the tool element 16" as well, a vertical projection 232 of same onto the projection plane 234 in the removal position is smaller than in the operating position, as this is schematically shown in FIGS. 14 and 15. In this way, an overexpansion of the connecting site between the tissues 116 connected to one another is prevented in the removal position when removing the instrument 12.

Another embodiment of a second tool element, which is provided as a whole with the reference number 16''', is shown in FIGS. 16 through 19. It can be used in the instrument 12 instead of the previously described second tool elements 16, 16' and 16".

The second tool element 16''' has an essentially plate-like design and comprises a disk 300. Disk 300 is provided in its center with a transversely running, oblong, oval slot 302. A hole 304 passes through the disk 300 somewhat laterally offset to its center, which lies in the area of the slot 302. A mounting pin 306, which likewise passes through the slot 302, is inserted adapted to rotate in unison into the hole 304. A distal end of a holding member 84''', which has a sleeve-like design, protrudes into the area of the slot 302. On the side proximally from its end 308, the holding member 84''' is provided with a hole 310, whose inside diameter is adapted to the outside diameter of the mounting pin 306 so that the mounting pin 306 is rotatable in same in relation to the hole 310. All in all, this then makes possible a pivoting of the disk 300 about a longitudinal axis defined by the mounting pin 306.

A folding mechanism 312, which couples the disk 300 via a connecting rod 314 in an articulated manner with a distal end 316 of a force transmission element 318, is used for the forcibly actuated pivoting of the disk 300. The force transmission element 318 has an extended, rod-shaped section 320, whose proximal end 322 can be coupled with the force transmission member 80. The end 316 is thickened in a head-shaped manner against the section 320 and shaped almost cuboid. On one side of same is formed a lateral open slot 324. Further, a cross hole 326 is provided, which passes through the slot 323 transversely. A mounting pin 328 is inserted adapted to rotate in unison into the cross hole 326. The rod-shaped connecting rod 314 is likewise provided with a hole 330 and is mounted pivotably on the mounting pin 328. Adjacent to an opposite end of the connecting rod 314 is provided another hole 332. It is used for mounting the connecting rod 314 on another mounting pin 334. This is inserted into another hole 336 of the disk 300. The hole 336 is oriented parallel to the hole 304 and arranged outside the slot 302 adjacent to an edge 338 of the disk 300, and lying opposite the hole 304 in relation to the longitudinal axis 54. Starting from the edge 338, a groove 342, into which the end of the connection rod 314 with its hole 332 dips, is provided on a top side 340 of the disk 300. In this way, the connecting rod 314 is mounted in an articulated manner on the mounting pin 334. Thus, the connecting rod 314 with an end at the second tool element 16''' acts on a point of action or hinge point, which is spaced away from the pivot axis 344 defined by the longitudinal axis of the mounting pin 306.

The folding mechanism 312 is actuated by the force transmission element 318 being moved in the distal direction. The result of this is that the connecting rod 314 is bent in relation to the disk 300. The further the force transmission member 318 is moved in the distal direction, the further the connecting rod 314 draws the area of the disk 300 in the distal direction, at which the groove 342 is provided. In an extreme position, the disk 300 is then aligned almost parallel to the longitudinal axis 54. All in all, it is thus also possible in the second tool element 16''' to embody a removal position, in which a vertical projection 232 of same onto the projection plane 234, which runs at right angles to the longitudinal axis 54, is smaller than in the operating position.

An RF electrode 29 may likewise be arranged or formed at the second tool element 16''' in a form as described above in the second tool element 16. As an alternative, it is also conceivable to provide a self-contained, circular electrode, which is not divided into electrode segments. Similar to how the second tool element 16'' comprises the electrode element 282, electrode elements may likewise be provided in second tool elements 16' and 16''', for example, in the form of the electrode element 282 or else even the electrode element 52.

As already mentioned above in connection with the second tool element 16', the RF electrodes provided at the second tool elements 16'' and 16''' may usually be connected to the RF terminal contacts 50 by providing corresponding electrically conductive connections at the instrument 12.

All above-described first and second tool elements 14, 16, 16', 16'', 16''', as well as 138 and 140 are preferably composed of either electrically conductive or electrically insulating components. Also conceivable are components, which are partly electrically conductive or partly electrically insulating. The components themselves may especially be produced completely from electrically conductive or electrically insulating materials, whereby the electrically insulating components may also be produced from an electrically conductive material, which is especially provided with an electrically insulating outer shell or coating.

Especially plastics, which still have sufficient strength at the temperatures occurring during the use of the surgical system 10, may be used as electrically insulating or nonconductive materials. For example, both thermoplasts and duroplasts are suitable. As an alternative, ceramic material may also be used as insulating material. The components of the tool elements 14, 16, 16', 16'', 16''', as well as 138 and 140 may especially be made of a ceramic. A ceramic to be used has especially the advantage over many plastics that it also has a sufficient stability at very high temperatures. The RF electrodes 28 and 29 are preferably made of a metal or a metal alloy. As an alternative, the use of electrically conductive ceramics is also conceivable for forming the RF electrodes 28 and 29, provided that they meet the requirements of the application of RF current.

The tool elements 14, 16, 16', 16'', 16''', as well as 138 and 140 may, for example, be produced as described below. The individual parts, units or components of the tool elements 14, 16, 16', 16'', 16''', as well as 138 and 140 may especially be produced separately and then be joined together, for example, by bonding. As an alternative, it is, for example, also possible to insert the electrically conductive parts of the RF electrodes 28 and 29 as inserts into a plastics injection molding die and to injection-mold with a plastic. As already mentioned, the electrodes may be made from a metal or an electrically conductive ceramic. In a segmenting of the RF electrodes 28 and 29 as described above, a corresponding number of electrically conductive electrode segments made of a metal or a metal alloy or an electrically conductive ceramic must, for example, then be inserted into the plastics injection molding die before injection molding with a suitable plastic.

In a purely ceramic design of the tool elements 14, 16, 16', 16'', 16''', as well as 138 and 140, a ceramic powder injection molding process is offered, e.g., the so-called "2K CIM" technology, a two-component micro-ceramic powder injection molding process. Here, two different ceramics are injected in an injection molding process, which form the electrically conductive and electrically insulating parts in the finished tool elements 14, 16, 16', 16'', 16''', as well as 138 and 140. After the injection molding, two different ceramics are sintered together. They may be, for example, an $Al_2O_3$ ceramic and a mixed ceramic made of $Al_2O_3$ and TiN.

The invention claimed is:

1. A surgical instrument for connecting body tissue with two tool elements, which are movable in relation to one another and which comprise an RF electrode each, each RF electrode defining a minimal distance from one another in a position of proximity of the tool elements, lie opposite one another and point towards one another, whereby at least one of the RF electrodes is divided into at least two electrode segments, and in that the at least two electrode segments are electrically insulated from each other, wherein
    each of the tool elements defines a flat tool element surface defining a plane, said flat tool element surface containing one of the RF electrodes positioned flush within said plane of said tool element surface without protruding from said plane;
    the at least two electrode segments are arranged next to one another and define at least two rows of electrodes;
    at least one electrode segment has a first electrode segment section, which is part of a first row of electrodes, and a second electrode segment section, which is part of a second row of electrodes; and the RF electrode, which can be fed current in segments, defines an electrode center line, and electrode segments adjacent to one another are arranged offset to one another in a direction defined by the electrode center line, such that the sum of the lengths of all electrode segments is greater than the electrode length.

2. A surgical instrument in accordance with claim 1, wherein the electrode segments, lying opposite one another and pointing towards one another in the position of proximity, form a pair of electrode segments.

3. A surgical instrument in accordance with claim 2, wherein the electrode segments forming the pair of electrode segments are the same size or essentially the same size.

4. A surgical instrument in accordance with claim 1, wherein the at least one RF electrode divided into at least two electrode segments defines an electrode length, and wherein each of the at least two electrode segments defines a segment length that is shorter than the electrode length.

5. A surgical instrument in accordance with claim 1, wherein the tool elements comprise a first tool element and a second tool element, and wherein the instrument has a shaft at the distal end of which the first tool element is arranged or formed, and the second tool element comprises an electrode element that is movable in the shaft direction and is movable towards and away from the first tool element.

6. A surgical instrument in accordance with claim 5, wherein contact members pointing in the direction of the second tool element, which can be brought into electrically conductive contact with the electrode segments of the second tool element in a tissue connection position and are spaced away from the electrode segments of the second tool element in a tissue gripping position, protrude at the shaft and/or at the first tool element.

7. A surgical system comprising:
   the surgical instrument of claim 1; and
   at least one RF current generator, which can be selectively connected in an electrically conductive manner to the RF electrodes and/or to a cutting element.

8. A surgical system in accordance with claim 7, comprising at least one control and/or regulating means with a switching means for the sequential application of RF current to the electrode segments of at least one RF electrode.

9. A surgical system in accordance with claim 8, comprising an RF current generator, which can be selectively connected in an electrically conductive manner to the RF electrodes and/or to the cutting element and comprises the control and/or regulating means.

10. A surgical system in accordance with claim 8, wherein the control and/or regulating means is designed such that a current feed intensity and/or a duration of current feed can be adjusted for the individual electrode segments.

11. A surgical system in accordance with claim 8, wherein the control and/or regulating means comprises a temperature measuring means for measuring an electrode segment temperature and/or a tissue temperature.

12. A surgical system in accordance with claim 7, comprising a control and/or regulating means with a switching means for the simultaneous application of RF current to at least two electrode segments of at least one RF electrode.

13. A surgical system in accordance with claim 12, wherein at least one other electrode segment is arranged between the at least two electrode segments.

14. A control process for a surgical instrument in accordance with claim 1, wherein RF current is applied to one of the at least two electrode segments and at least one other of the at least two electrode segments is left currentless.

15. A control process in accordance with claim 14, wherein at least two electrode segments are fed current simultaneously.

16. A control process in accordance with claim 14, wherein electrode segments adjacent to one another are fed current one after the other.

17. A process for connecting two body tissues, using a surgical instrument according to claim 1, in which the two body tissues to be connected are held in contact with one another between two RF electrodes, of which at least one electrode is divided into at least two electrode segments, which electrode segments are electrically insulated from each other, and in which the body tissues are welded to one another by means of RF current along a connecting line by applying RF current to the at least two electrode segments.

18. A process in accordance with claim 17, wherein the RF current is applied to the at least two electrode segments one after the other.

19. A process in accordance with claim 17, wherein the RF electrodes predetermine the connecting line.

* * * * *